United States Patent
Burgey et al.

(10) Patent No.: US 7,659,264 B2
(45) Date of Patent: Feb. 9, 2010

(54) CGRP RECEPTOR ANTAGONISTS

(75) Inventors: Christopher S. Burgey, Philadelphia, PA (US); James Z. Deng, Eagleville, PA (US); Craig Potteiger, Reading, PA (US); Theresa M. Williams, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 329 days.

(21) Appl. No.: 11/664,905

(22) PCT Filed: Oct. 5, 2005

(86) PCT No.: PCT/US2005/035654

§ 371 (c)(1),
(2), (4) Date: Apr. 6, 2007

(87) PCT Pub. No.: WO2006/041830

PCT Pub. Date: Apr. 20, 2005

(65) Prior Publication Data

US 2008/0070899 A1    Mar. 20, 2008

Related U.S. Application Data

(60) Provisional application No. 60/616,911, filed on Oct. 7, 2004.

(51) Int. Cl.
C07D 403/12 (2006.01)
C07D 403/14 (2006.01)
A61K 31/55 (2006.01)

(52) U.S. Cl. .................................. 514/212.08; 540/524
(58) Field of Classification Search ............ 514/212.08; 540/524
See application file for complete search history.

(56) References Cited

FOREIGN PATENT DOCUMENTS

WO    WO 2005/000807    1/2005

*Primary Examiner*—Bruck Kifle
(74) *Attorney, Agent, or Firm*—William Krovatin; John C. Todaro

(57) ABSTRACT

The present invention is directed to compounds of Formula I: Formula I: I and Formula II: (where variables $R^1$, $R^2$, $R^3$, $R^4$, A, B, J, Q, T, V, W, X and Y are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

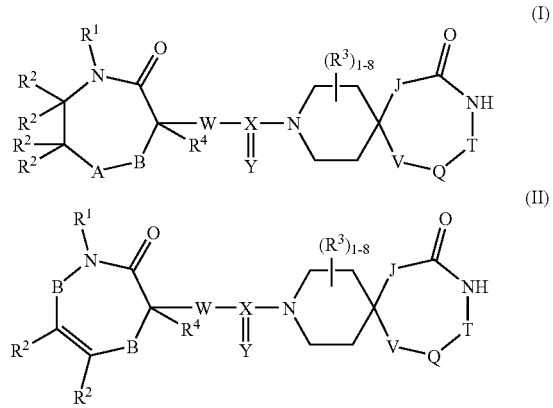

7 Claims, No Drawings

CGRP RECEPTOR ANTAGONISTS

RELATED APPLICATION DATA

This is a National filing under 35 USC 371 of PCT/US2005/035654, filed Oct. 5, 2005, which claims priority from U.S. Ser. No. 60/616,911 filed Oct. 7, 2004.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent vasodilator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187). CGRP activates receptors on the smooth muscle of intracranial vessels, leading to increased vasodilation, which is thought to be the major source of headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyper-reactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358) morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache. Compelling evidence of the efficacy of CGRP antagonists for the treatment of migraine has been provided by clinical studies using intravenously administered BIBN4096BS. This CGRP antagonist was found to be a safe and effective acute treatment for migraine (Olesen et al., N. Engl. J. Med., 2004, 350(11), 1104-1110).

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of Formula I:

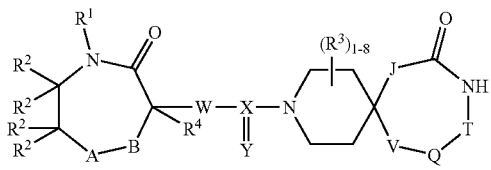

and Formula II:

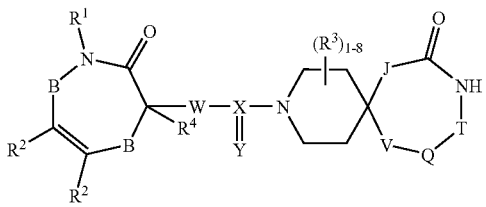

(where variables $R^1$, $R^2$, $R^3$, $R^4$, A, B, J, Q, T, V, W, X and Y are as defined herein) useful as antagonists of CGRP receptors and useful in the treatment or prevention of diseases in which the CGRP is involved, such as headache, migraine and cluster headache. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to CGRP antagonists which include compounds of Formula I:

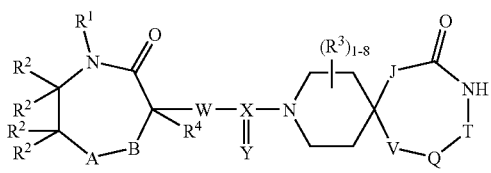

wherein:

A is a bond, $C(R^2)_2$, O, $S(O)_m$ or $NR^2$;

B is $(C(R^2)_2)_n$;

$R^1$ is selected from:
1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$;
2) aryl or heteroaryl, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$,
   p) $SO_2 NR^{10}R^{11}$,
   q) $N(R^{10})SO_2 R^{11}$,
   r) $S(O)_m R^{10}$,
   s) CN,
   t) $NR^{10}R^{11}$,
   u) $N(R^{10})(CO)NR^4 R^{11}$, and
   v) $O(CO)R^4$;

$R^2$ is independently selected from:
1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $(CO)NR^{10}R^{11}$,
   l) $O(CO)NR^{10}R^{11}$,
   m) $N(R^4)(CO)NR^{10}R^{11}$,
   n) $N(R^{10})(CO)R^{11}$,
   o) $N(R^{10})(CO)OR^{11}$, p) SO$_2$NR$^{10}$R$^{11}$,
q) N(R$^{10}$)SO$_2$R$^{11}$,
r) S(O)$_m$R$^{10}$,
s) CN,
t) NR$^{10}$R$^{11}$,
u) N(R$^{10}$)(CO)NR$^4$R$^{11}$, and
v) O(CO)R$^4$;

2) aryl or heteroaryl, unsubstituted or substituted with one or more substituents independently selected from:
a) C$_{1-6}$ alkyl,
b) C$_{3-6}$ cycloalkyl,
c) aryl, unsubstituted or substituted with 1-5 substituents each independently selected from R$^4$,
d) heteroaryl, unsubstituted or substituted with 1-5 substituents each independently selected from R$^4$,
e) heterocycle, unsubstituted or substituted with 1-5 substituents each independently selected from R$^4$,
f) (F)$_p$C$_{1-3}$ alkyl,
g) halogen,
h) OR$^4$,
i) O(CH$_2$)$_s$OR$^4$,
j) CO$_2$R$^4$,
k) (CO)NR$^{10}$R$^{11}$,
l) O(CO)NR$^{10}$R$^{11}$,
m) N(R$^4$)(CO)NR$^{10}$R$^{11}$,
n) N(R$^{10}$)(CO)R$^{11}$,
o) N(R$^{10}$)(CO)OR$^{11}$,
p) SO$_2$NR$^{10}$R$^{11}$,
q) N(R$^{10}$)SO$_2$R$^{11}$,
r) S(O)$_m$R$^{10}$,
s) CN,
t) NR$^{10}$R$^{11}$,
u) N(R$^{10}$)(CO)NR$^4$R$^{11}$, and
v) O(CO)R$^4$;

or, any two independent R$^2$ on the same or adjacent atoms join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

R$^{10}$ and R$^{11}$ are each independently selected from: H, C$_{1-6}$ alkyl, (F)$_p$C$_{1-6}$ alkyl, C$_{3-6}$ cycloalkyl, aryl, heteroaryl, and benzyl, unsubstituted or substituted with halogen, hydroxy or C$_1$-C$_6$ alkoxy, or R$^{10}$ and R$^{11}$ join to form a ring selected from: azetidinyl, pyrrolidinyl, piperidinyl, piperazinyl and morpholinyl, which ring is unsubstituted or substituted with 1-5 substituents each independently selected from R$^4$;

R$^4$ is selected from: H, C$_{1-6}$ alkyl, (F)$_p$C$_{1-6}$ alkyl, C$_{3-6}$ cycloalkyl, aryl, heteroaryl and benzyl, unsubstituted or substituted with halogen, hydroxy or C$_1$-C$_6$ alkoxy;

W is O, NR$^4$ or C(R$^4$)$_2$;

X is C or S;

Y is O, (R$^4$)$_2$, NCN, NSO$_2$CH$_3$ or NCONH$_2$, or Y is O$_2$ when X is S;

R$^6$ is independently selected from H and:
a) C$_{1-6}$ alkyl,
b) C$_{3-6}$ cycloalkyl,
c) aryl, unsubstituted or substituted with 1-5 substituents each independently selected from R$^4$,
d) heteroaryl, unsubstituted or substituted with 1-5 substituents each independently selected from R$^4$,
e) heterocycle, unsubstituted or substituted with 1-5 substituents each independently selected from R$^4$,
f) (F)$_p$C$_{1-3}$ alkyl,
g) halogen,
h) OR$^4$,
i) O(CH$_2$)$_s$OR$^4$,
j) CO$_2$R$^4$,
k) (CO)NR$^{10}$R$^{11}$,
l) O(CO)NR$^{10}$R$^{11}$,
m) N(R$^4$)(CO)NR$^{10}$R$^{11}$,
n) N(R$^{10}$)(CO)R$^{11}$,
o) N(R$^{10}$)(CO)OR$^{11}$,
p) SO$_2$NR$^{10}$R$^{11}$,
q) N(R$^{10}$)SO$_2$R$^{11}$,
r) S(O)$_m$R$^{10}$,
s) CN,
t) NR$^{10}$R$^{11}$,
u) N(R$^{10}$)(CO)NR$^4$R$^{11}$, and
v) O(CO)R$^4$;

J is a bond, C(R$^6$)$_2$, O, or NR$^6$;

V is a bond, C(R$^6$)$_2$, O, S(O)$_m$, NR$^6$, C(R$^6$)$_2$—C(R$^6$)$_2$, C(R$^6$)=C(R$^6$), C(R$^6$)$_2$—N(R$^6$), C(R$^6$)=N, N(R$^6$)—C(R$^6$)$_2$, N=C(R$^6$) or N(R$^6$)—N(R$^6$);

Q is selected from: =C(R$^{7a}$)—, —C(R$^{7a}$)$_2$—, —C(=O)—, —S(O)$_m$—, =N— and —N(R$^{7a}$)—;

T is selected from: =C(R$^{7b}$)—, —C(R$^{7b}$)$_2$—, —C(=O)—, —S(O)$_m$—, =N— and —N(R$^{7b}$)—;

R$^3$ is independently selected from H, substituted or unsubstituted C$_1$-C$_3$ alkyl, F, CN and CO$_2$R$^4$;

R$^{7a}$ and R$^{7b}$ are each independently selected from R$^2$, where R$^{7a}$ and R$^{7b}$ and the atom(s) to which they are attached optionally form a ring selected from C$_{3-6}$ cycloalkyl, aryl, heterocycle, and heteroaryl, which ring is unsubstituted or substituted with 1-10 substituents each independently selected from R$^6$;

p is 0 to 2q+1, for a substituent with q carbons;

m is 0, 1 or 2;

n is 0 or 1;

s is 1, 2 or 3;

and pharmaceutically acceptable salts and individual diastereomers thereof.

Further embodiments of the invention are CGRP antagonists of Formula I which include compounds of the Formula Ia:

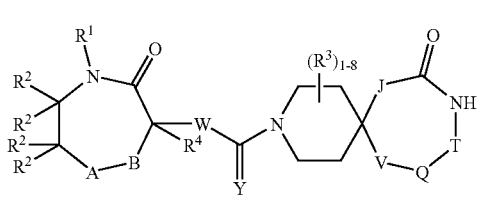

wherein:

A is a bond, C(R$^2$)$_2$, O, S(O)$_m$ or NR$^2$;

B is (C(R$^2$)$_2$)$_n$;

Y is O or NCN;

n is 0 or 1;

$R^1, R^2, R^4, W, Y, R^3, J, Q, T, V$, and m are as defined in Formula I;

and pharmaceutically acceptable salts and individual stereoisomers thereof.

Still further embodiments of the invention are CGRP antagonists of Formula I which include compounds of the Formula Ib:

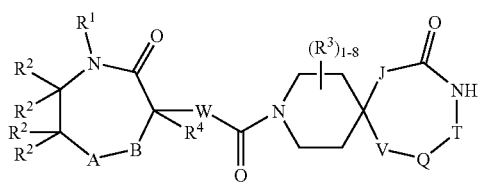

Ib wherein:

A is a bond, $C(R^2)_2$, O, $S(O)_m$ or $NR^2$;

B is $(C(R^2)_2)_n$;

n is 0 or 1;

$R^1, R^2, R^4, W, R^3, J, Q, T, V$, and m are as defined in Formula I;

and pharmaceutically acceptable salts and individual stereoisomers thereof.

Additional embodiments of the invention are CGRP antagonists of Formula I which include compounds of the Formula Ic:

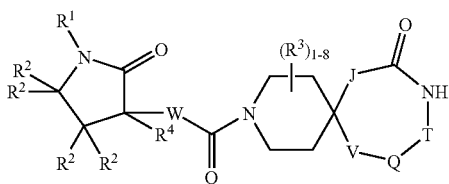

Ic wherein:

$R^1, R^2, R^4, W, R^3, J, Q, T, V$, and m are as defined in Formula I;

and pharmaceutically acceptable salts and individual stereoisomers thereof.

Additional embodiments of the invention are CGRP antagonists of Formula I which also include compounds of the Formula Id:

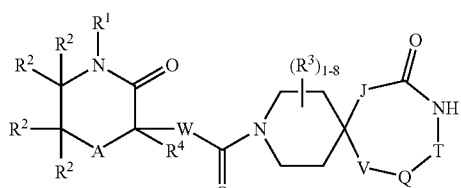

Id wherein:

A is $C(R^2)_2$, O, $S(O)_m$ or $NR^2$;

$R^1, R^2, R^4, W, R^3, J, Q, T, V$, and m are as defined in Formula I;

and pharmaceutically acceptable salts and individual stereoisomers thereof.

Additional embodiments of the invention are CGRP antagonists of Formula I which include compounds of the Formula Ie:

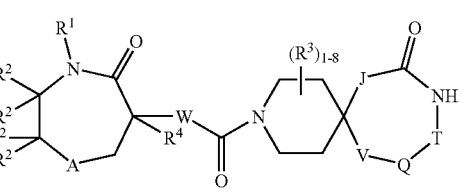

Ie wherein:

A is $C(R^2)_2$, O, $S(O)_m$ or $NR^2$;

$R^1, R^2, R^4, W, R^3, J, Q, T, V$, and m are defined in Formula I;

and pharmaceutically acceptable salts and individual stereoisomers thereof.

Further embodiments of the invention are CGRP antagonists of Formulae Ia-Ie, wherein:

$R^1$ is selected from:
1) H, $C_1$-$C_6$ alkyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10}R^{11}$, and
   m) $O(CO)R^4$; and
2) aryl or heteroaryl, unsubstituted or substituted with one or more substituents each independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and,
   m) $O(CO)R^4$;

$R^2$ is selected from:
1) H, $C_0$-$C_6$ alkyl, $C_2$-$C_6$ alkynyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) $S(O)_m R^4$,
   l) CN,
   m) $NR^{10}R^{11}$, and
   n) $O(CO)R^4$; and
2) aryl or heteroaryl, unsubstituted or substituted with one more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$, and
   m) $O(CO)R^4$,
   or, any two independent $R^2$ on the same or adjacent atoms join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

$R^{10}$ and $R^{11}$ are independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

$R^6$ is independently selected from H and:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2 R^4$,
   g) $(CO)NR^{10}R^{11}$,
   h) $SO_2 NR^{10}R^{11}$,
   i) $N(R^{10})SO_2 R^{11}$,
   j) $S(O)_m R^4$,
   k) CN,
   l) $NR^{10}R^{11}$ and
   m) $O(CO)R^4$; and J is a bond, $C(R^5)_2$, O, $S(O)_m$ or $NR^5$, and V is a bond, $C(R^6)_2$, O, $S(O)_m$, $NR^6$, $C(R^6)_2$—$C(R^6)_2$, $C(R^6)$=$C(R^6)$, $C(R^6)_2$—N($R^6$), $C(R^6)$=N, $N(R^6)$—$C(R^6)_2$, N=$C(R^6)$ or $N(R^6)$—N($R^6$), such that when:
   J is a bond and V is a bond and T is C(=O)— the following structure forms:

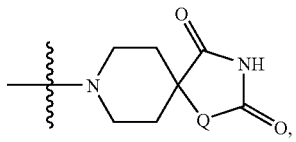

J is a bond and V is a bond the following structure forms:

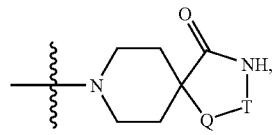

J is a bond the following structure forms:

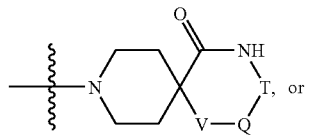

, or

V is a bond the following structure forms:

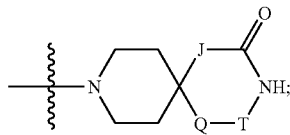

Q is selected from:
   (1) =$C(R^{7a})$—,
   (2) —$C(R^{7a})_2$—,
   (3) —C(=O)—,
   (4) —$S(O)_m$—,
   (5) =N—, and
   (6) —$N(R^{7a})$—;

T is selected from:
   (1) =$C(R^{7b})$—,
   (2) —$C(R^{7b})_2$—,
   (3) —C(=O)—,
   (4) —$S(O)_m$—,
   (5) =N—, and
   (6) —$N(R^{7b})$—;

$R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom(s) to which they are attached optionally join to form a ring selected from $C_{3-6}$cycloalkyl, aryl, heterocycle, and heteroaryl, which ring is unsubstituted or substituted with 1-10 substituents each independently selected from $R^6$;

p is 0 to 2q+1, for a substituent with q carbons m is 0 to 2;

s is 1 to 3;

and pharmaceutically acceptable salts and individual stereoisomers thereof.

Still further embodiments of the invention are CGRP antagonists of Formulae Ia-Ie, wherein:

$R^1$ is selected from:
1) H, $C_1$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$, where heteroaryl is selected from: imidazole, isoxazole, oxazole, pyrazine, pyrazole, pyridazine, pyridine, pyrimidine, and thiazole;
   e) heterocycle, unsubstituted or substituted with 1-5 substituents each independently selected from $R^4$, where heterocycle is selected from: azetidine, dioxane, dioxolane, morpholine, oxetane, piperazine, piperidine, pyrrolidine, tetrahydrofuran, and tetrahydropyran;
   f) $(F)_pC_{1-3}$ alkyl,
   g) halogen,
   h) $OR^4$,
   i) $O(CH_2)_sOR^4$,
   j) $CO_2R^4$,
   k) CN,
   l) $NR^{10}R^{11}$,
   m) $O(CO)R^4$;
2) aryl or heteroaryl, selected from: phenyl, imidazole, isoxazole, oxazole, pyrazine, pyrazole, pyridazine, pyridine, pyrimidine, and thiazole, unsubstituted or substituted with one or more substituents each independently selected from:
   a) $C_{1-6}$ alkyl,
   b) $C_{3-6}$ cycloalkyl,
   c) $(F)_pC_{1-3}$ alkyl,
   d) halogen,
   e) $OR^4$,
   f) $CO_2R^4$,
   g) $(CO)NR^{10}R^{11}$,
   h) $SO_2NR^{10}R^{11}$,
   i) $N(R^{10})SO_2R^{11}$,
   j) $S(O)_mR^4$,
   k) CN,
   l) $NR^{10}R^{11}$, and
   m) $O(CO)R^4$;

$R^2$ is selected from:
1) H, $C_0$-$C_6$ alkyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) phenyl, unsubstituted or substituted with 1-5 substituents each independently selected from $R^4$,
   d) heteroaryl, unsubstituted or substituted with 1-5 substituents each independently selected from $R^4$, where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;
   e) heterocycle, unsubstituted or substituted with 1-5 substituents each independently selected from $R^4$, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;
   f) $(F)_pC_{1-3}$ alkyl,
   g) halogen,
   h) $OR^4$,
   i) $O(CH_2)_sOR^4$,
   j) $CO_2R^4$,
   k) CN,
   l) $NR^{10}R^{11}$, and
   m) $O(CO)R^4$; and
2) aryl or heteroaryl, selected from: phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole, where said aryl or heteroaryl is unsubstituted or substituted with one or more substituents each independently selected from:
   a) $C_{1-6}$ alkyl,
   b) $C_{3-6}$ cycloalkyl,
   c) $(F)_pC_{1-3}$ alkyl,
   d) halogen,
   e) $OR^4$,
   f) $CO_2R^4$,
   g) $(CO)NR^{10}R^{11}$,
   h) $SO_2NR^{10}R^{11}$,
   i) $N(R^{10})SO_2R^{11}$,
   j) $S(O)_mR^4$,
   k) CN,
   l) $NR^{10}R^{11}$, and
   m) $O(CO)R^4$,
   or, any two independent $R^2$ on the same or adjacent atoms join to form a ring selected from cyclobutyl, cyclopentenyl, cyclopentyl, cyclohexenyl, cyclohexyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyrrolyl, pyrrolinyl, morpholinyl, thiomorpholine, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl;

$R^{10}$ and $R^{11}$ are each independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally joined to form a ring selected from: azetidinyl, pyrrolidinyl, piperidinyl, piperazinyl and morpholinyl, which is unsubstituted or substituted with 1-5 substituents each independently selected from $R^4$;

$R^4$ is independently selected from: H, $C_{1-6}$ alkyl, $(F)_pC_{1-6}$ alkyl, $C_{3-6}$ cycloalkyl, aryl, heteroaryl and phenyl, unsubstituted or substituted with hydroxy or $C_1$-$C_6$ alkoxy;

W is $NR^4$ or $C(R^4)_2$;

J is a bond, V is a bond, Q is —N($R^{7a}$)—, and T is —C(=O)—, such that the following structure forms:

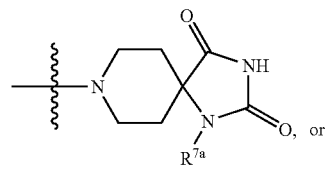

J is a bond, V is a bond, Q is —N=, and T is =C($R^{7b}$)—, such that the following structure forms:

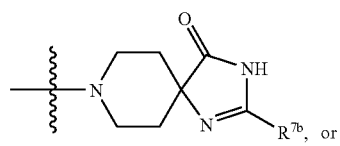

J is a bond, V is a bond, Q is —C($R^{7a}$)$_2$—, and T is —C($R^{7b}$)$_2$—, such that the following structure forms:

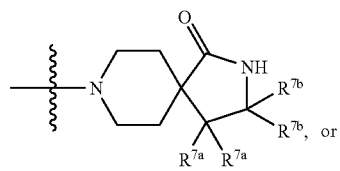

J is a bond, V is a bond, Q is —C($R^{7a}$)=, T is =C($R^{7b}$)—, and the atoms to which $R^{7a}$ and $R^{7b}$ are attached are joined together to form a benzene, pyridine, or diazine ring such that a structure selected from:

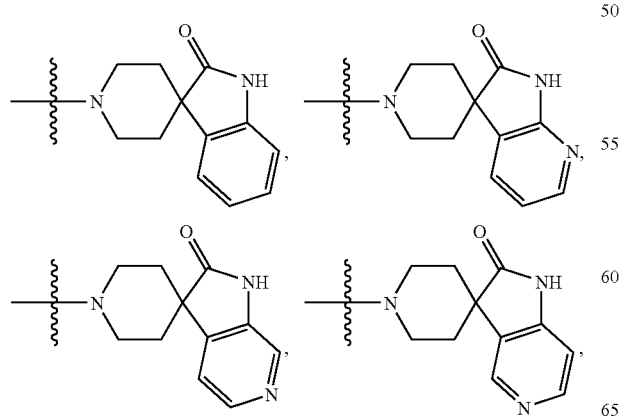

-continued

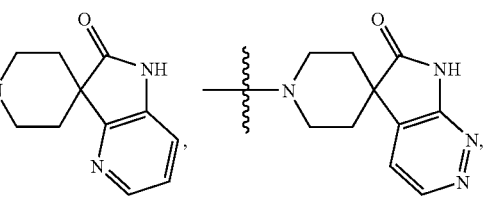

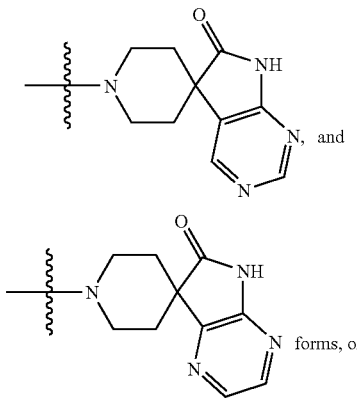

J is a bond, V is C($R^{6a}$)$_2$, Q is —C($R^{7a}$)=, T is =C($R^{7b}$)—, and the atoms to which $R^{7a}$ and $R^{7b}$ are attached are joined together to form a benzene, or pyridine ring such that a structure selected from:

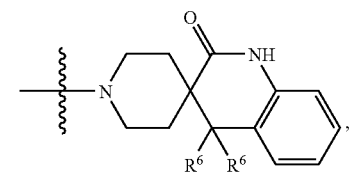

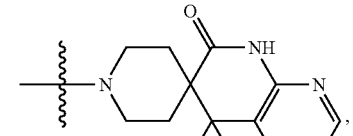

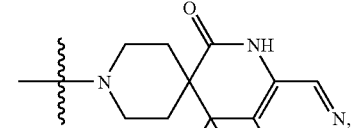

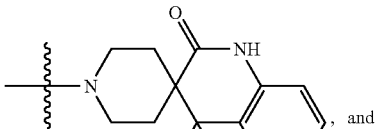

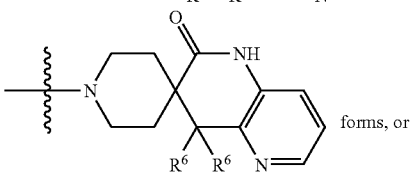

J is O, V is a bond, Q is —C(R$^{7a}$)=, T is =C(R$^{7b}$)—, and the atoms to which R$^{7a}$ and R$^{7b}$ are attached are joined together to form a benzene, or pyridine ring such that a structure selected from:

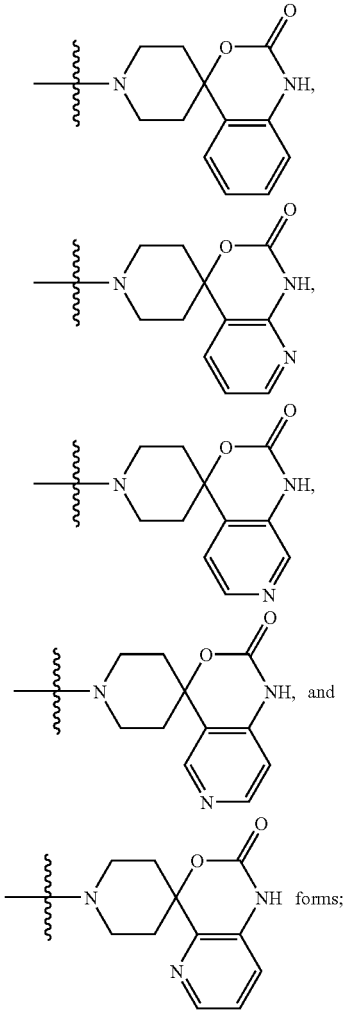

forms;

R$^6$ is independently selected from H and:
a) C$_{1-6}$ alkyl,
b) C$_{3-6}$ cycloalkyl,
c) (F)$_p$C$_{1-3}$ alkyl,
d) halogen,
e) OR$^4$,
f) CO$_2$R$^4$,
g) (CO)NR$^{10}$R$^{11}$,
h) SO$_2$NR$^{10}$R$^{11}$,
i) N(R$^{10}$)SO$_2$R$^{11}$,
j) S(O)$_m$R$^4$,
k) CN,
l) NR$^{10}$R$^{11}$, and
m) O(CO)R$^4$;

R$^3$ is independently selected from H, substituted or unsubstituted C$_1$-C$_3$ alkyl, F, CN and CO$_2$R$^4$;

R$^{7a}$ and R$^{7b}$ are each independently selected from R$^2$, where R$^{7a}$ and R$^{7b}$ and the atom(s) to which they are attached optionally join to form a ring selected from C$_{3-6}$cycloalkyl, aryl, heterocycle, and heteroaryl, which ring is unsubstituted or substituted with 1-10 substituents each independently selected from R$^6$;

p is 0 to 2q+1, for a substituent with q carbons m is 0 to 2;

s is 1 to 3;

and pharmaceutically acceptable salts and individual stereoisomers thereof.

Another embodiment of the invention includes CGRP antagonists which include compounds of Formula II:

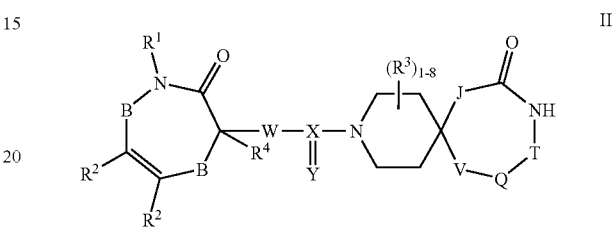

wherein:

B, J, Q, T, V, W, X, Y, R$^1$, R$^2$, R$^3$ and R$^4$ are as defined in Formula I, and pharmaceutically acceptable salts and individual diastereomers thereof.

It is to be understood that where one or more of the above recited structures or substructures recite multiple substituents having the same designation each such variable may be the same or different from each similarly designated variable.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The independent syntheses of these diastereomers or their chromatographic separations may be achieved as known in the art by appropriate modification of the methodology disclosed herein.

Their absolute stereochemistry may be determined by the x-ray crystallography of crystalline products or crystalline-intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not every substituent or combination of substituents which are said to form rings are capable of forming a ring structure in every circumstance or situation. Moreover, even those substituents capable of ring formation may or may not form a ring structure in every circumstance or situation.

Also as appreciated by those of skill in the art, halo or halogen as used herein are intended to include chloro, fluoro, bromo and iodo.

As used herein, "alkyl" is intended to mean linear, branched and cyclic structures having no double or triple bonds. Thus $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) Eur. J. Pharmacol. 415, 39-44). Briefly, membranes (25 µg) were incubated in 1 ml of binding buffer [10 mM HEPES, pH 7.4, 5 mM MgCl$_2$ and 0.2% bovine serum albumin (BSA)] containing 10 pM $^{125}$I-CGRP andantagonist. After incubation at room temperature for 3 h, the assay was terminated by filtration through GFB glass fibre filter plates (Millipore) that had been blocked with 0.5% polyethyleneimine for 3 h. The filters were washed three times with ice-cold assay buffer, then the plates were air dried. Scintillation fluid (50 µl) was added and the radioactivity was counted on a Topcount (Packard Instrument). Data analysis was carried out by using Prism and the K$_i$ was determined by using the Cheng-Prusoff equation (Cheng & Prusoff (1973) Biochem. Pharmacol. 22, 3099-3108).

NATIVE RECEPTOR FUNCTIONAL ASSAY: SK-N-MC cells were grown in minimal essential medium (MEM) supplemented with 10% fetal bovine serum, 2 mM L-glutamine, 0.1 mM non-essential amino acids, 1 mM sodium pyruvate, 100 units/ml penicillin and 100 µg/ml streptomycin at 37° C., 95% humidity, and 5% CO$_2$. For cAMP assays, cells were plated at 5×10$^5$ cells/well in 96-well poly-D-lysine-coated plates (Becton-Dickinson) and cultured for ~18 h before assay. Cells were washed with phosphate-buffered saline (PBS, Sigma) then pre-incubated with 300 µM isobutylmethylxanthine in serum-free MEM for 30 min at 37° C. Antagonist was added and the cells were incubated for 10 min before the addition of CGRP. The incubation was continued for another 15 min, then the cells were washed with PBS and processed for cAMP determination according to the manufacturer's recommended protocol. Maximal stimulation over basal was defined by using 100 nM CGRP. Dose-response curves were generated by using Prism. Dose-ratios (DR) were calculated and used to construct full Schild plots (Arunlakshana & Schild (1959) Br. J. Pharmacol. 14, 48-58).

RECOMBINANT RECEPTOR: Human CRLR (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 ug/ml streptomycin, and maintained at 37° C. and 95% humidity. Cells were subcultured by treatment with 0.25% trypsin with 0.1% EDTA in HBSS. Stable cell line generation was accomplished by co-transfecting 10 ug of DNA with 30 ug Lipofectamine 2000 (Invitrogen) in 75 cm$^2$ flasks. CRLR and RAMP1 expression constructs were co-transfected in equal amounts. Twenty-four hours after transfection the cells were diluted and selective medium (growth medium+300 ug/ml hygromycin and 1 ug/ml puromycin) was added the following day. A clonal cell line was generated by single cell deposition utilizing a FACS Vantage SE (Becton Dickinson). Growth medium was adjusted to 150 ug/ml hygromycin and 0.5 ug/ml puromycin for cell propagation.

RECOMBINANT RECEPTOR BINDING ASSAY: Cells expressing recombinant human CRLR/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 10 ug of membranes were incubated in 1 ml binding buffer (10 mM HEPES, pH 7.4, 5 mM MgCl$_2$, and 0.2% BSA) for 3 hours at room temperature containing 10 pM $^{125}$I-hCGRP (Amersham Biosciences) and antagonist. The assay was terminated by filtration through 96-well GFB glass fiber filter plates (Millipore) that had been blocked with 0.05% polyethyleneimine. The filters were washed 3 times with ice-cold assay buffer (10 mM HEPES, pH 7.4). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \%I_{max}/100)}{1 + ([Drug]/K_i(1 + [Radiolabel]/K_d)^{nH}}$$

Where Y is observed CPM bound, $Y_{max}$ is total bound counts, Y min is non specific bound counts, (Y max–Y min) is specific bound counts, % I max is the maximum percent inhibition, % 1 min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 mM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; Amersham Biosciences). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_1$ or $IC_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-$HT_{1B/1D}$ agonist, for example sumatriptan, naratriptan, zolmitriptan, eletriptan, almotriptan, frovatriptan, donitriptan, and rizatriptan, a 5-$HT_{1D}$ agonist such as PNU-142633 and a 5-$HT_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrine precursor; anti-anxiety agents such as diazepam, alprazolam, chlordiazepoxide and chlorazepate; serotonin 5$HT_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocomine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases.

As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

The synthesis of intermediates and final compounds may be conducted as described in Schemes 1-12.

Reaction Schemes

The preparation of final compounds proceeds through intermediates such as those of Formula III and Formula IV, and representative syntheses are described herein.

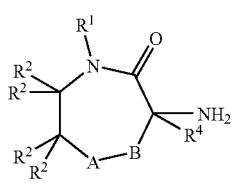

-continued

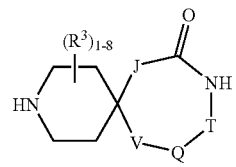

In general, intermediates of the Formulae III and IV can be coupled through a urea linkage as shown in Scheme 1. Amine intermediate 1 can be converted to a reactive carbamate, for example p-nitrophenylcarbamate 2, which is subsequently reacted with an amine like that of intermediate 3 to produce urea 4. Other activated intermediates known to those skilled in the art can be used to prepare compounds like 4. For example, amine 1 can be directly acylated with the appropriate carbamoyl chloride.

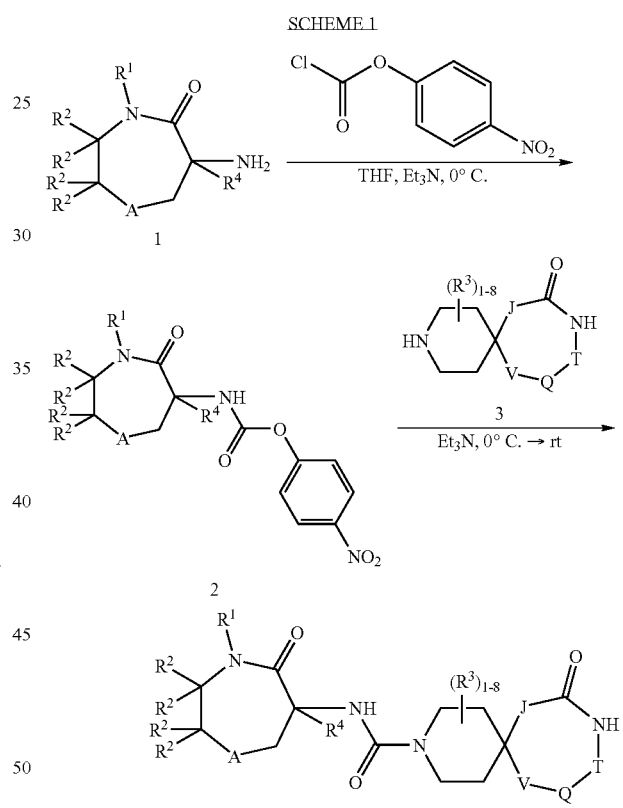

A representative synthesis of a spirolactam intermediate is shown in Scheme 2, using a spiroazaoxindole example. 7-Azaindole 5 may be protected with a variety of protecting groups, such as the (trimethylsilyl)ethoxymethyl group shown in Scheme 2. Following the method of Marfat and Carter (*Tetrahedron Lett.*, 1987, 28, 4027-4030), treatment of 6 with pyridine hydrobromide perbromide provides the dibromoazaoxindole 7, which may be reduced to the corresponding azaoxindole 8 by reaction with zinc. Alkylation of 8 with cis-1,4-dichloro-2-butene is carried out using cesium carbonate in DMF to afford the spiroazaoxindole 9. Removal of the SEM protecting group under standard conditions followed by osmium tetroxide catalyzed dihydroxylation provides the diol intermediate 11. Periodate oxidative cleavage of the diol, followed by a double reductive amination (*Org. Lett.*, 2000, 26, 4205-4208) affords the spiropiperidine 12. The methodology shown in Scheme 2 is not limited to aza-oxindoles such as 12, but may be applied to a variety of suitably protected heterocyclic systems to give the corresponding spiro compounds.

action of sodium hexamethyldisilazide and di-tert-butyl dicarbonate. Ortho metalation according to Davies (*Tetrahedron Lett.*, 2004, 45, 1721-1724) and addition of the resultant anion to N-benxyloxycarbonyl-4-piperidinone, gives, after in situ cyclization, product 15. Final deprotection and dechlorination under standard hydrogenolysis conditions gives the intermediate 16.

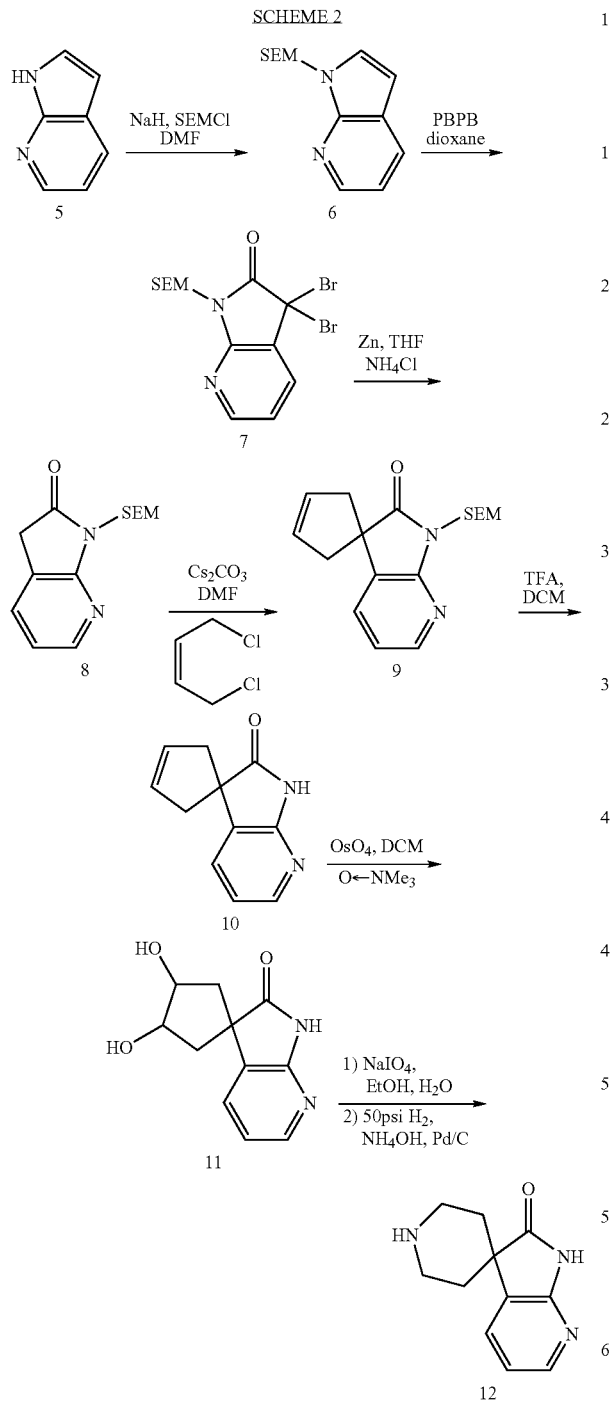

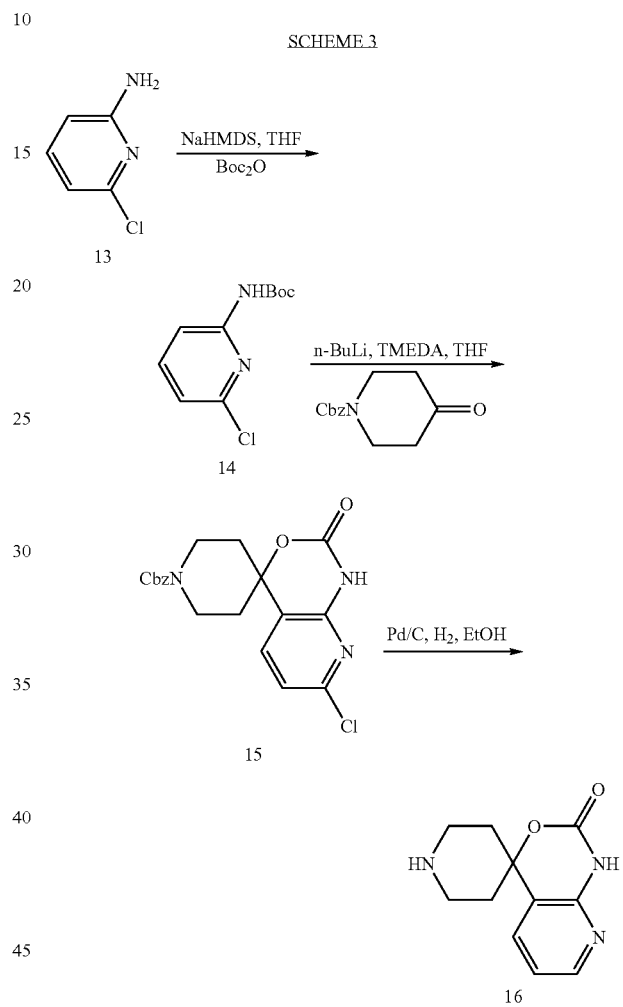

The synthesis of the related spiropyridobenzoxazinone can be accomplished according to Scheme 3. 2-Amino-6-chloropyridine 13 can be protected as its Boc derivative under the Deprotonation of N-Boc-4-piperidinecarboxylic acid methyl ester 17 with potassium hexamethyldisilazide and subsequent alkylation with allyl bromide affords 18 (Scheme 4). Oxidative cleavage of the terminal double bond provides aldehyde 19 which is condensed with 2-methyl-2-propanesulfinamide to give imine 20. Addition of phenyllithium to the imine is accompanied by ring closure to 21. Removal of the protecting groups with HCl in methanol gives compounds like 22.

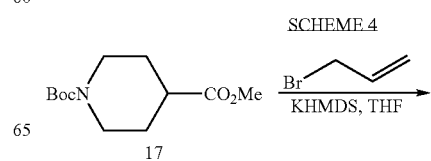

In Scheme 5, the anion of N-Boc-4-carbethoxypiperidine can be alkylated to afford compounds such as 24. The nitro and chloro groups of the resulting product 24 can be reduced under standard hydrogenation conditions to give aniline 25. Ring closure with acetic acid followed by final deprotection under standard conditions gives the desired spiropiperidine product 27.

In Scheme 6, Wittig reaction of the 4-ketopiperidine 28 gives the α,β-unsaturated ester 29. The resulting product 29 can be isomerized to the α,β-unsaturated ester 30 under basic conditions (*Tetrahedron Lett*, 2004, 4401-4404). Trimethylaluminum mediated amidation with 2-amino-3-bromopyridine followed by amide alkylation with 2-(trimethylsilyl)ethoxymethyl chloride affords the product 32. The key palladium-mediated spirocyclization can be affected through the Fu modification (*J Amer Chem Soc*, 2001, 6989-7000) of the Heck reaction. A two-stage deprotection with concomitant double bond reduction under standard conditions gives the desired spironaphthyridinone 34.

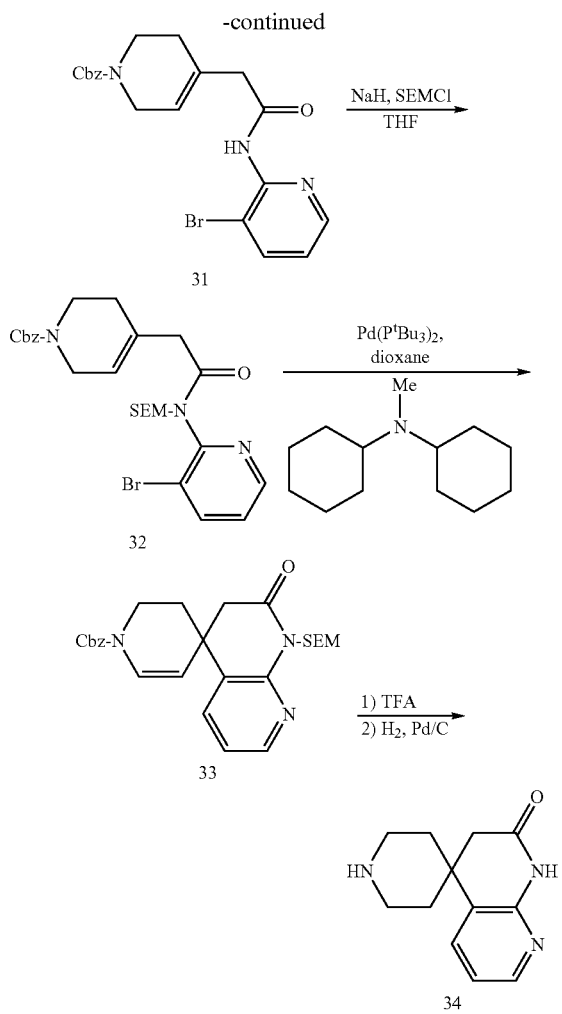

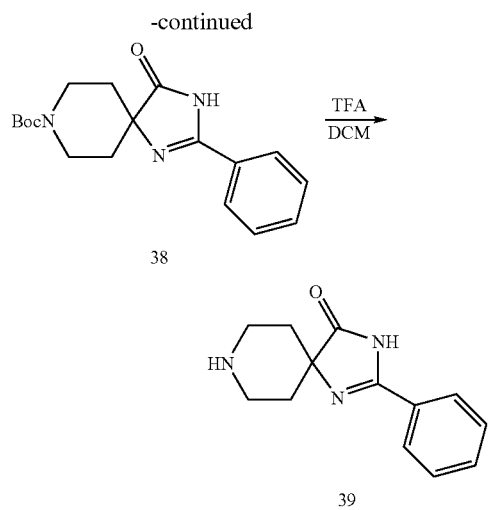

The aminoester 35 can be converted to the primary amide 36 with a standard peptide coupling agent, such as EDC (Scheme 7). Hydrogenolysis of the Cbz group, followed by condensation with trimethyl orthobenzoate and concomitant ring closure affords the product 38. Standard deprotection cycle 39.

Caprolactams can be assembled following an olefin metathesis strategy as outlined in Scheme 8. 2,4-Dimethoxybenzylamine hydrochloride is alkylated with 2,3-dibromopropene under mild basic conditions to give amine 41. (2R)-2-{[(benzyloxy)carbonyl]amino}pent-4-enoic acid 42, prepared in one step from commercially available D-allyl glycine according to known procedures (J. Chem. Soc., 1962, 3963-3968), can be coupled to amine 41 under a variety of conditions to give amide 43. A variety of transition metal catalyzed cross couplings can be performed on the vinyl bromide, for example palladium-mediated arylations with phenylboronic acid and sodium carbonate, yielding styrene derivative 44. Ring-closing metathesis occurs in the presence of the Grubbs second generation ruthenium catalyst in dichloromethane with mild heating to afford lactam 45. Removal of the dimethoxybenzyl group and hydrogenation with in situ protection of the primary amine gives the corresponding saturated lactam 47. After selective alkylation of the amide nitrogen with various electrophiles such as alkyl bromides, deprotection under acidic conditions yields compounds of the general formula 49.

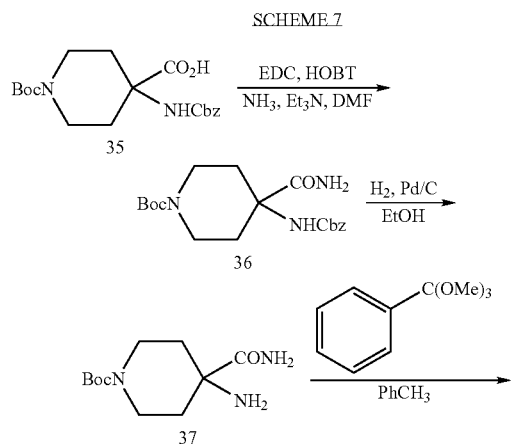

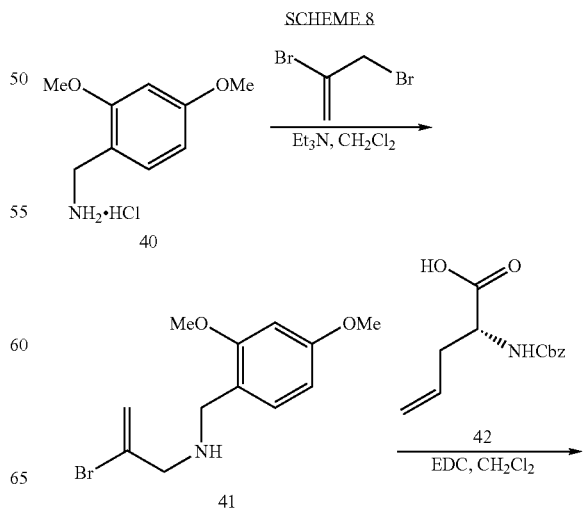

-continued

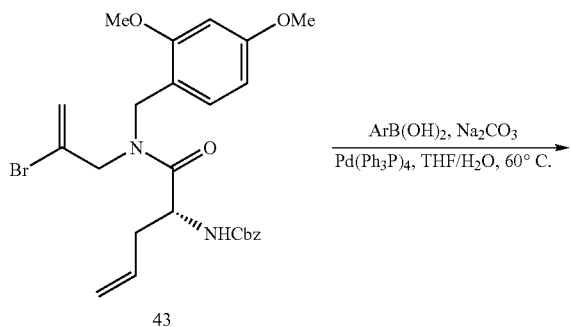
43

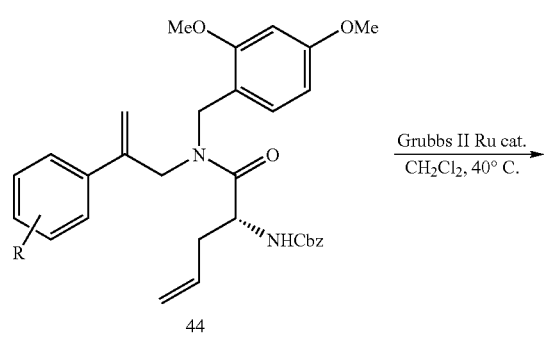
44

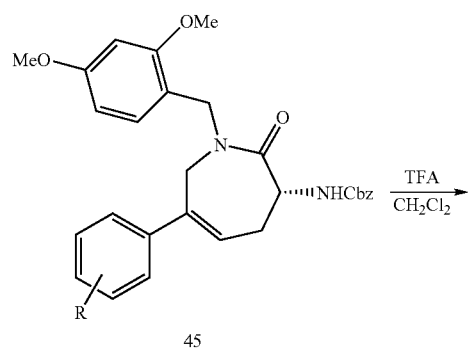
45

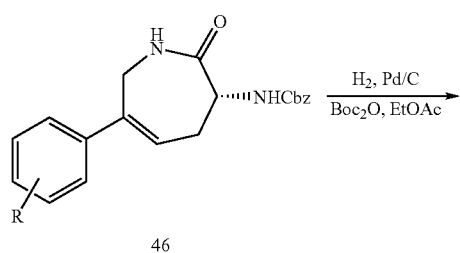
46

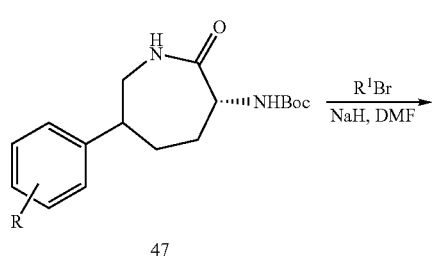
47

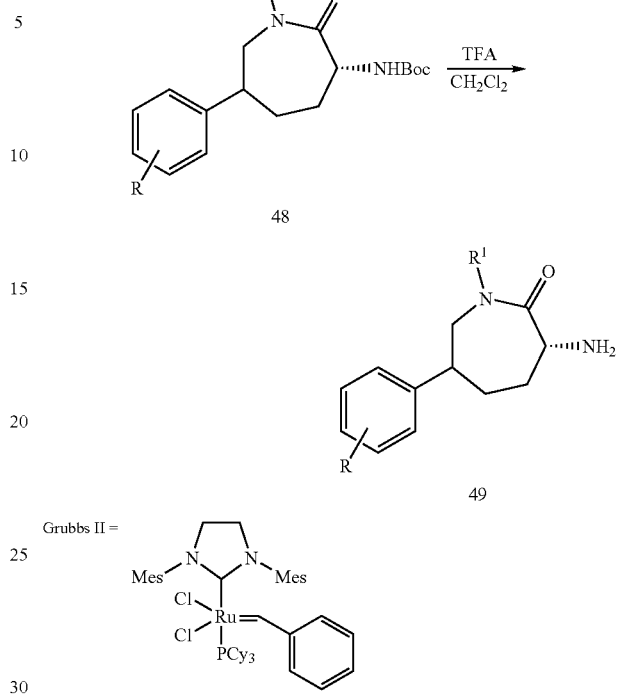
48

49

Grubbs II =

Alternatively, a C6-aryl group can be introduced as outlined in Scheme 9. Addition of nitromethane to the known glutamic acid derived aldehyde 50 (*Tetrahedron Asymmetry*, 1998, 3381-94), followed by in situ elimination affords nitro olefin 51. Addition of the aryl group via a boronic acid derivative, or similar equivalent, can be accomplished in a stereoselective manner through chiral ligand-Rh catalysis. Concomitant nitro reduction and benzyl ester hydrogenolysis affords the amino acid 53. Ring closure under standard conditions, followed by removal of a single tert-butoxycarbonyl group furnishes the 47 45. Intermediates such as 53 can be further processed as in Scheme 10.

SCHEME 9

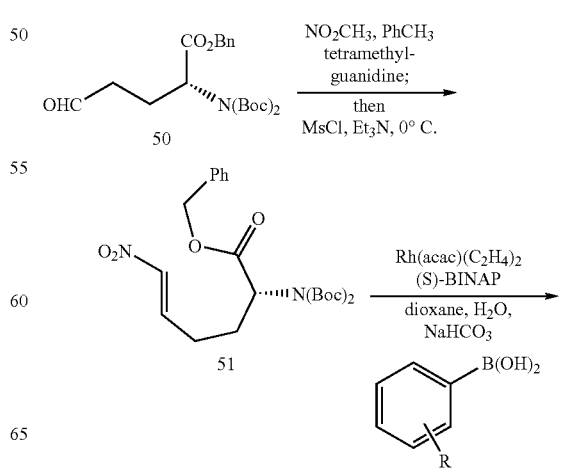

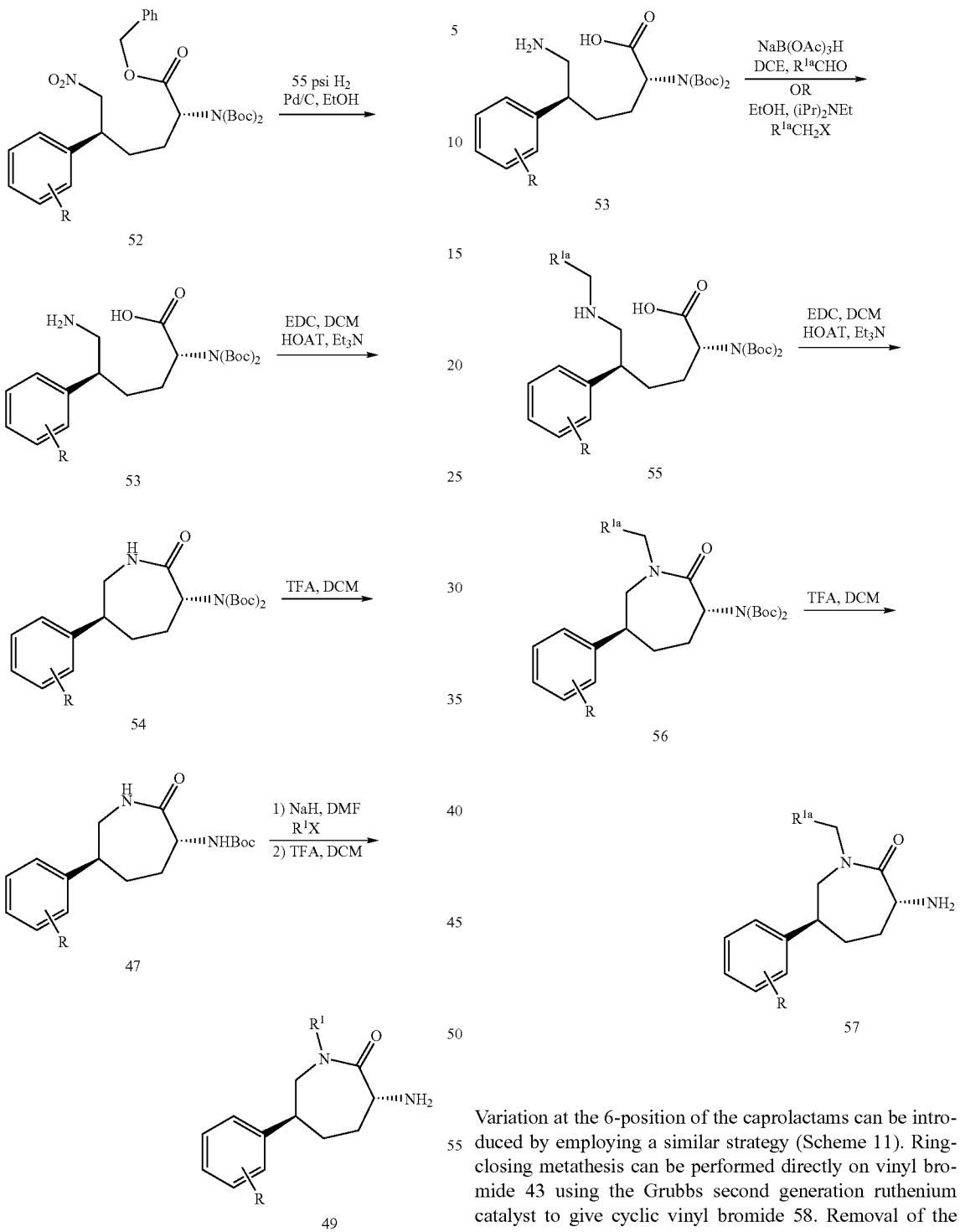

Alternatively, amino acid 53 can be alkylated, either reductively or via an $S_N2$ displacement, to afford intermediates such as 55 (Scheme 10). Ring closure under standard conditions, followed by protecting group removal furnishes the lactam 57.

Variation at the 6-position of the caprolactams can be introduced by employing a similar strategy (Scheme 11). Ring-closing metathesis can be performed directly on vinyl bromide 43 using the Grubbs second generation ruthenium catalyst to give cyclic vinyl bromide 58. Removal of the dimethoxybenzyl group and palladium-mediated cross coupling, in this case with a boronic acid, furnishes compounds of the general formula 60. The transformation of 59 to 60 is not limited to boronic acid derivatives. After standard hydrogenation, the amide nitrogen can be selectively alkylated with various electrophiles, for example alkyl bromides, using sodium hydride as base. Deprotection yields lactams of the general formula 63.

SCHEME 11

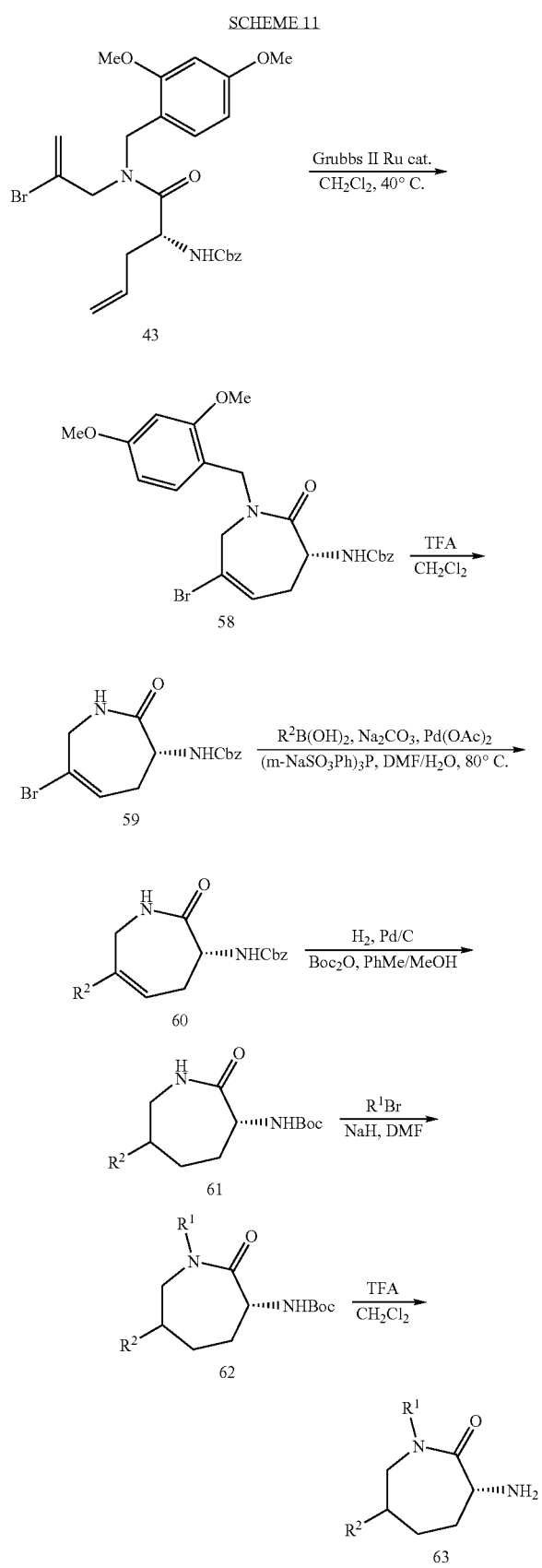

Alternatively, addition of a Grignard or similar reagent, to the nitro olefin 51 followed by nitro reduction and benzyl ester hydrogenolysis affords various amino acids such as 65 (Scheme 12). Ring closure with EDC furnishes caprolactam 66. Final deprotection with trifluoroacetic acid gives the product 67.

SCHEME 12

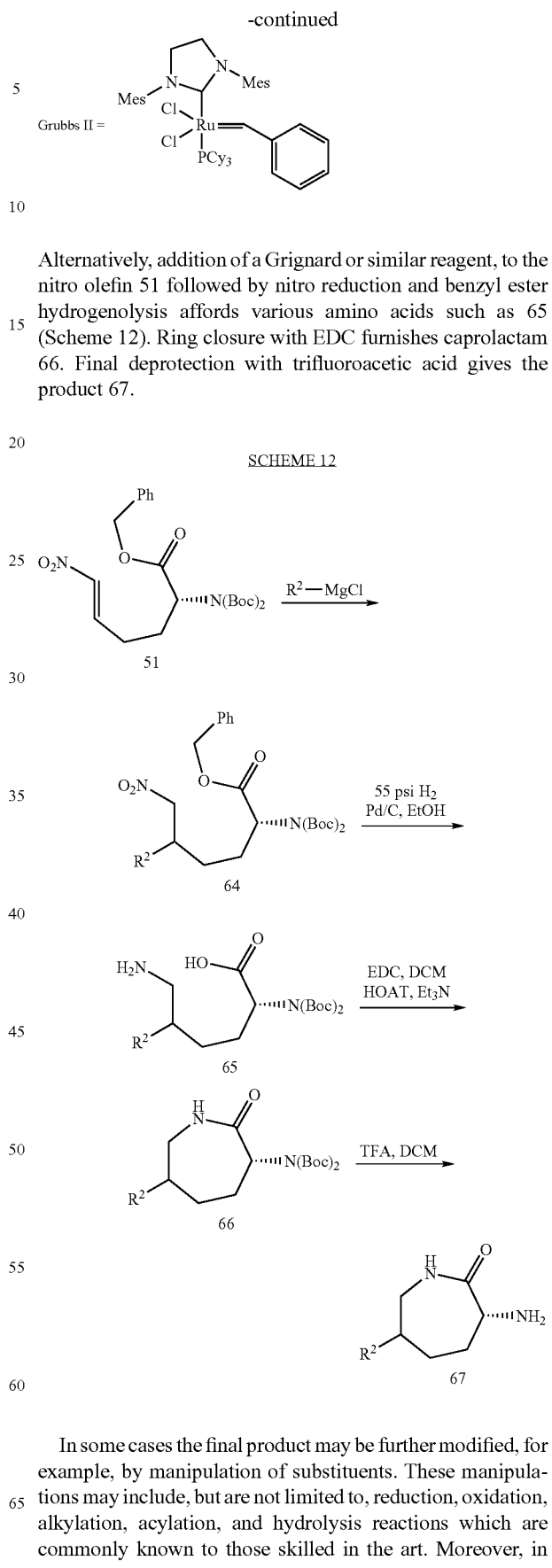

In some cases the final product may be further modified, for example, by manipulation of substituents. These manipulations may include, but are not limited to, reduction, oxidation, alkylation, acylation, and hydrolysis reactions which are commonly known to those skilled in the art. Moreover, in

INTERMEDIATES AND EXAMPLES

The following examples are provided so that the invention might be more fully understood. These examples are illustrative only and should not be construed as limiting the invention in any way.

INTERMEDIATE 1

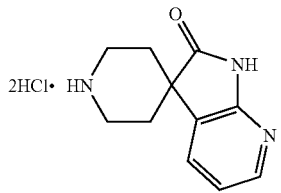

Spiro[piperidine-4,3'-pyrrolo[2,3-b]pyridin]-2'(1'H)-one dihydrochloride

Step A. 1-{[2-Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with H$_2$O (500 mL) and the mixture was extracted with CH$_2$Cl$_2$ (5×300 mL). The combined organic layers were washed with brine, dried over MgSO$_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.174 mol) in dioxane (300 mL) was added dropwise over 30 min to a suspension of pyridine hydrobromide perbromide (277 g, 0.868 mol) in dioxane (300 mL). The reaction was stirred at ambient temperature using an overhead mechanical stirrer. After 60 min, the biphasic reaction mixture was quenched with H$_2$O (300 mL) and extracted with EtOAc. The aqueous layer was washed with EtOAc (2×300 mL) and the combined organic layers were washed with H$_2$O (4×300 mL; the final wash was pH 5-6), then brine (300 mL), then dried over MgSO$_4$, filtered and concentrated under reduced pressure. The crude product was immediately dissolved in CH$_2$Cl$_2$ and the solution filtered through a plug of silica, eluting with CH$_2$Cl$_2$ until the dark red color had completely eluted from the plug. The filtrate was washed with saturated aqueous NaHCO$_3$ (400 mL), then brine (400 mL), dried over MgSO$_4$ and concentrated in vacuo to give the title compound. MS: m/z=423 (M+1).

Step C. 1-{[2-(Trimethylsilyl)ethoxy]meth}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one from Step B (65 g, 0.154 mol) in THF (880 mL) and saturated aqueous ammonium chloride (220 mL). After 3 h, the reaction was filtered and concentrated in vacuo. The residue was partitioned between EtOAc and H$_2$O which resulted in the formation of a white precipitate. Both layers were filtered through a Celite pad and the layers were separated. The aqueous layer was washed with EtOAc (2×) and the combined organic layers were washed with H$_2$O, dried over MgSO$_4$, filtered, and concentrated. The crude product was filtered through a plug of silica gel eluting with CH$_2$Cl$_2$:EtOAc—90:10 and the eluant was concentrated under reduced pressure to provide the title compound. MS: m/z=265 (M+1).

Step D. spiro[cyclopent-3-ene-1,3'-pyrrolo[2,3-b]pyridin]-2'(1'H)-one

To a solution of cis-1,4-dichloro-2-butene (1.98 g, 15.8 mmol) and 1-{[2-(trimethylsilyl)ethoxy]methyl}-1,3-dihydro-2H-pyrrolo[2,3-b]pyridin-2-one (3.49 g, 13.2 mmol) in DMF (175 mL) was added cesium carbonate (10.7 g, 32.9 mmol). After 24 h the reaction mixture was partitioned between Et$_2$O (200 mL) and H$_2$O (200 mL). The aqueous layer was extracted further with Et$_2$O (2×200 mL). The combined organic layers were washed with H$_2$O (2×100 mL), then brine (100 mL), dried over MgSO$_4$, filtered, and concentrated under reduced pressure. To a solution of this material in dichloromethane (150 mL) was added trifluoroacetic acid (150 mL). After 1 h, the reaction was concentrated, dissolved in EtOH (150 mL) and 2N HCl (150 mL) was added. This mixture was heated at 45° C. for 48 h. The mixture was concentrated, diluted with saturated aqueous NaHCO$_3$, and extracted with dichloromethane (2×). The combined organic layers were dried and concentrated. The crude product was purified by silica gel chromatography, eluting with a gradient of 0 to 5% methanol:dichloromethane to give the title compound (0.62 g). MS: m/z=187.1 (M+1).

Step E. 3,4-dihydroxyspiro[cyclopentane-1,3'-pyrrolo[2,3-b]pyridin]-2'(1'H)-one To a mixture of trimethylamine-N-oxide dihydrate (408 mg, 3.67 mmol) and spiro[cyclopent-3-ene-1,3'-pyrrolo[2,3-b]pyridin]-2'(1'H)-one (622 mg, 3.34 mmol) in dichloromethane (115 mL) was added osmium tetroxide (25 uL of 2.5% solution in 2-methyl-2-propanol). After 24 h the reaction mixture was concentrated. The crude product was loaded onto a silica gel chromatography column with a minimal amount of methanol and eluted with a gradient of 5 to 20% methanol:dichloromethane to give the title compound (0.63 g). MS: m/z=221.0 (M+1).

Step F. tert-butyl 2'-oxo-1',2'-dihydro-1H-spiro[piperidine-4,3'-pyrrolo[2,3-b]pyridine]-1-carboxylate To a mixture of 3,4-dihydroxyspiro[cyclopentane-1,3'-pyrrolo[2,3-b]pyridin]-2'(1'H)-one (640 mg, 2.91 mmol) in 3:1 ethanol:water (160 mL) was added sodium periodate (622 mg, 2.91 mmol). Upon consumption of the starting material, ammonium hydroxide (50 mL) was slowly added to the reaction mixture. Palladium hydroxide (200 mg, 20%) was added and the reaction was hydrogenated at 50 psi. After 24 h, 200 mg of palladium hydroxide was added and the hydrogenation continued for an additional 24 h. The reaction mixture was filtered through celite and concentrated. This material was dissolved in DMF (10 mL) and di-tert-butyl dicarbonate (635 mg, 2.91 mmol) was added followed by triethylamine (0.811 mL, 5.82 mmol). After 24 h, the reaction was diluted with saturated aqueous NaHCO₃ and extracted with ether (3×). The combined organic layers were washed with water (3×), dried and concentrated. The crude product was purified by silica gel chromatography, eluting with a gradient of 0 to 10% methanol:dichloromethane to give the title compound (489 mg). MS: m/z=304.1 (M+1).

Step G. Spiro[piperidine-4,3'-pyrrolo[2,3-b]pyridin]-2'(1'H)-one dihydrochloride tert-Butyl 2'-oxo-1',2'-dihydro-1H-spiro[piperidine-4,3'-pyrrolo[2,3-b]pyridine]-1-carboxylate (451 mg, 1.49 mmol) was dissolved in ethyl acetate (3 mL) and a solution of 4N hydrochloric acid in dioxane (7.5 mmol) was added at room temperature. After 24 h, the volatiles were removed in vacuo, to give the title compound (404 mg). MS 204.1 (M+1). ¹H NMR (500 MHz, CD₃OD) δ 8.31 (d, J=7.1 Hz, 1H), 8.20 (d, J=6.1 Hz, 1H), 7.45 (dd, J=6.8, 6.8 Hz, 1H), 3.74 (brdd, 2H), 3.47 (brdd, 2H), 2.35 (brddd, 2H), 2.21 (brd, 2H).

extracted with EtOAc (3×). The combined organic layers were washed with H₂O, brine, dried over MgSO₄, filtered, and concentrated under reduced pressure. The crude product was purified by silica gel chromatography, eluting with a gradient of 25 to 50% ethyl acetate:hexane to give the title compound (0.160 g). MS: m/z=338.0 (M+1).

Step C. Spiro[piperidine-4,4'-pyrido[2,3-d][1,3]oxazin]-2'(1'H)-one

10% Palladium on carbon (300 mg) was added to a solution of benzyl 7'-chloro-2'-oxo-1',2'-dihydro-1H-spiro[piperidine-4,4'-pyrido[2,3-d][1,3]oxazine]-1-carboxylate (1.85 g, 1.77 mmol) in EtOH (250 mL). The reaction vessel was evacuated and back-filled with nitrogen (3×), then back-filled with hydrogen (1 atm). After 24 h, the mixture was filtered though celite and concentrated to give the title compound (1.07 g). MS 220.1 (M+1). ¹H NMR (500 MHz, CD₃OD) δ 8.26 (dd, J=1.7, 5.0 Hz, 1H), 7.69 (dd, J=1.6, 7.7 Hz, 1H), 7.16 (dd, J=5.0, 7.7 Hz, 1H), 3.49-3.42 (m, 4H), 2.38-2.25 (m, 4H).

INTERMEDIATE 2

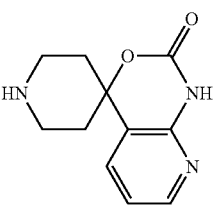

Spiro[piperidine-4,4'-pyrido[2,3-d][1,3]oxazin]-2'(1'H)-one

Step A. tert-Butyl (6-chloropyridin-2-yl)carbamate

To a solution of 2-amino-6-chloropyridine (5.24 g, 40.8 mmol) and sodium hexamethyldisilazide (1.0 M, 89.8 mL, 89.8 mmol) in THF (35 mL) was added a solution of di-tert-butyl dicarbonate (9.80 g, 44.9 mmol) in THF (35 mL). After 24 h the reaction was concentrated and the residue was partitioned between EtOAc (30 mL) and 1N HCl (100 mL). The aqueous layer was extracted further with EtOAc (2×). The combined organic layers were washed with NaHCO₃, dried over MgSO₄, filtered, and concentrated under reduced pressure. The crude product was purified by silica gel chromatography, eluting with a gradient of 20 to 100% dichloromethane:hexane to give the title compound (7.73 g). MS: m/z=173.0 (M–ᵗBu).

Step B. Benzyl 7'-chloro-2'-oxo-1',2'-dihydro-1H-spiro[piperidine-4,4'-pyrido[2,3-d][1,3]oxazine]-1-carboxylate To a –20° C. solution of N,N,N',N'-tetramethylethylenediamine (0.335 g, 2.89 mmol) in THF (1 mL) was added n-butyllithium (2.5M, 1.15 mL, 2.89 mmol) over 10 min. After 30 min, the mixture was cooled to –78° C. and tert-butyl (6-chloropyridin-2-yl)carbamate (0.300 g, 1.31 mmol) in THF (0.8 mL) was added over 15 min. After 1 h, the reaction was warmed to –50° C., stirred for 2 h and then N-benxyloxycarbonyl-4-piperidinone (0.459 g, 1.97 mmol) in THF (1 mL) was added over 10 min. The reaction was allowed to warm to room temperature and then stirred for 24 h. A solution of saturated aqueous NaHCO₃ was added and the mixture

INTERMEDIATE 3

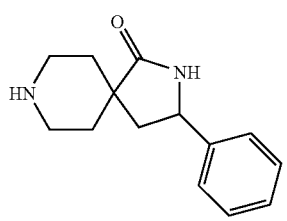

3-Phenyl-2,8-diazaspiro[4.5]decan-1-one dihydrochloride

Step A. 1-tert-butyl 4-methyl 4-allylpiperidine-1,4-dicarboxylate

To a –78° C. solution of N-Boc-4-piperidinecarboxylic acid methyl ester (5.70 g, 23.4 mmol) in THF (80 mL) was added potassium hexamethyldisilazide (0.5 M in toluene, 70.2 mL, 35.1 mmol). After 2 h allyl bromide (6.69 mL, 77.3 mmol) was added, the reaction stirred at this temperature for 0.5 h, then warmed to 0° C. After 3 h the reaction was quenched by the addition of saturated aqueous ammonium chloride and extracted with dichloromethane (3×). The combined organic layers were dried over MgSO₄, filtered, and concentrated under reduced pressure. The crude product was purified by silica gel chromatography, eluting with a gradient of 0 to 8% methanol:dichloromethane to give the title compound (6.0 g). MS: m/z=284.2 (M+1).

Step B. 1-tert-butyl 4-methyl 4-(2-oxoethyl)piperidine-1,4-dicarboxylate

Ozone was bubbled through a –78° C. solution of 1-tert-butyl 4-methyl 4-allylpiperidine-1,4-dicarboxylate (4.0 g, 14.1 mmol) in 3:1 dichloromethane:methanol over 30 min to produce a blue solution. Nitrogen was bubbled through the reaction mixture for 30 min, then dimethylsulfide (5.2 mL, 70.6 mmol) was added and the reaction warmed to room temperature. After 3 h, the reaction mixture was concentrated under reduced pressure. The crude product was purified by silica gel chromatography, eluting with a gradient of 5 to 50% ethyl acetate:hexane to give the title compound (1.72 g). MS: m/z 230.1 (M–tBu).

Step C. 1-tert-butyl 4-methyl 4-{(2E)-2-[(tert-butyl-sulfinyl)imino]ethl}piperidine-1,4-dicarboxylate A solution of 1-tert-butyl 4-methyl 4-(2-oxoethyl)piperidine-1,4-dicarboxylate (822 mg, 2.88 mmol), copper(II) sulfate (1.38 g, 8.64 mmol) and 2-methyl-2-propanesulfinamide (354 mg, 3.17 mmol) in dichloroethane (15 mL) was heated at 65° C. for 24 h. The reaction was cooled, filtered and concentrated. The residue was partitioned between saturated aqueous NaHCO$_3$ and dichloromethane, separated, the organic layer dried over MgSO$_4$, and concentrated. The crude product was purified by silica gel chromatography, eluting with a gradient of 0 to 7% methanol:dichloromethane to give the title compound (0.9 g). MS: m/z=389.2 (M+1).

Step D. tert-butyl 2-(tert-butylsulfinyl)-1-oxo-3-phenyl-2,8-diazaspiro[4.5]decane-8-carboxylate To a −78° C. solution of 1-tert-butyl 4-methyl 4-{(2E)-2-[(tert-butylsulfinyl)imino]ethyl}piperidine-1,4-dicarboxylate (358 mg, 0.921 mmol) in ether (10 mL) was added phenyllithium (1.8 M, 1.6 mL, 3.1 mmol). The reaction was warmed to 0° C. After 1 h the reaction was quenched by the addition of saturated aqueous ammonium chloride and extracted with dichloromethane (3×). The combined organic layers were dried over MgSO$_4$, filtered, and concentrated under reduced pressure. The crude product was purified by silica gel chromatography, eluting with a gradient of 2 to 55% ethyl acetate:hexanes to give the title compound (50 mg). MS: m/z=435.2 (M+1).

Step E. 3-Phenyl-2,8-diazaspiro[4.5]decan-1-one dihydrochloride

To a solution of tert-butyl 2-(tert-butylsulfinyl)-1-oxo-3-phenyl-2,8-diazaspiro[4.5]decane-8-carboxylate (21 mg, 0.048 mmol) in methanol (4 mL) was added 4N HCl in dioxane (4 mL). After 24 h the reaction was concentrated give the title compound). MS: m/z=231.1 (M+1).

INTERMEDIATE 4

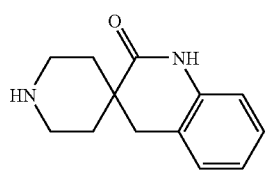

1',4'-dihydro-2'H-spiro[piperidine-4,3'-quinolin]-2'-one dihydrochloride

Step A. 1-tert-butyl 4-ethyl 4-(2-aminobenzyl)piperidine-1,4-dicarboxylate

10% Palladium on carbon (200 mg) was added to a solution of 1-tert-butyl 4-ethyl 4-(5-chloro-2-nitrobenzyl)piperidine-1,4-dicarboxylate (250 mg, 0.586 mmol) in EtOH (15 mL). The reaction vessel was evacuated and back-filled with nitrogen (3×), then back-filled with hydrogen (55 psi). After 24 h, the mixture was filtered though celite and concentrated to give the title compound (0.20 g). MS: m/z=363.1 (M+1).

Step B. tert-butyl 2'-oxo-1',4'-dihydro-1H,2H-spiro[piperidine-4,3'-quinoline]-1-carboxylate A solution of 1-tert-butyl 4-ethyl 4-(2-aminobenzyl)piperidine-1,4-dicarboxylate (200 mg, 0.552 mmol) in acetic acid (5 mL) was heated at 70° C. for 1 h. The reaction was concentrated and the residue was partitioned between saturated aqueous NaHCO$_3$ and dichloromethane, separated, the organic layer dried over MgSO$_4$, and concentrated. The crude product was purified by silica gel chromatography, eluting with a gradient of 0 to 5% methanol:dichloromethane to give the title compound (73 mg). MS: m/z=317.1 (M+1).

Step C. 1',4'-dihydro-2'H-spiro[piperidine-4,3'-quinolin]-2'-one dihydrochloride To a solution of tert-butyl 2'-oxo-1',4'-dihydro-1H,2'H-spiro[piperidine-4,3'-quinoline]-1-carboxylate (72 mg, 0.228 mmol) in dichloromethane (8 mL) was added trifluoroacetic acid (2 mL). After 2 h the reaction was concentrated, diluted with dichloromethane and 2M HCl in ether (3 equiv) and stirred for 2 h. The reaction was concentrated to give the title compound (60 mg). MS: m/z=217.1 (M+1).

INTERMEDIATE 5

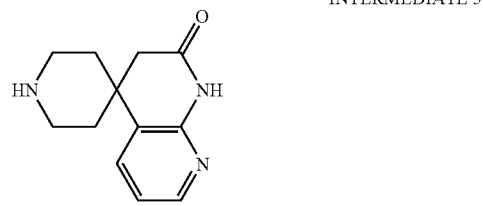

1H-Spiro[1,8-naphthyridine-4,4'-piperidin]-2(3H)-one

Step A. Benzyl 4-(2-methoxy-2-oxoethylidene)piperidine-1-carboxylate

A solution of N-benxyloxycarbonyl-4-piperidinone (5.0 g, 21.4 mol) and methyl (triphenylphosphoranylidene)acetate (10.0 g, 30.0 mmol) in benzene (100 mL) was heated at 75° C. for 48 h. The reaction was concentrated, diluted with ether, the precipitate filtered off, and the rinsate concentrated. The crude product was purified by silica gel chromatography, eluting with a gradient of 20 to 60% ethyl acetate:hexanes to give the title compound (5.25 g). MS: m/z=290.1 (M+1).

Step B. Benzyl 4-(2-methoxy-2-oxoethyl)-3,6-dihydropyridine-1(2H)-carboxylate A solution of benzyl 4-(2-methoxy-2-oxoethylidene)piperidine-1-carboxylate (5.25 g, 18.1 mol) and 1,8-diazabicyclo[5.4.0]undec-7-ene (2.71 mL, 18.1 mol) in DMF (120 mL) was stirred at room temperature. After 3 d the reaction was diluted with water and extracted with ether (4×). The organic washes were combined, dried over MgSO$_4$, filtered and concentrated under reduced pressure. The crude product was purified by silica gel chromatography, eluting with a gradient of 5 to 30% ethyl acetate:hexanes to give the title compound (2.44 g). MS: m/z=290.1 (M+1). $^1$H NMR (500 MHz, CDCl$_3$) δ 7.30-7.25 (m, 5H), 5.5 (brs, 1H), 5.2 (s, 2H), 4.0 (brs, 2H), 3.7 (s, 3H), 3.6 (brs, 2H), 3.0 (s, 2H), 2.2 (brs, 2H).

Step C. Benzyl 4-{2-[(3-bromopyridin-2-yl)amino]-2-oxoethyl}-3,6-dihydropyridine-1(2H)-carboxylate Timethylaluminum (2.0 M, 2.05 mL, 4.10 mol) was added slowly to a 0° C. solution of benzyl 4-(2-methoxy-2-oxoethyl)-3,6-dihydropyridine-1(2B)-carboxylate (0.79 g, 2.73 mol) and 2-amino-3-bromopyridine (0.520 g, 3.00 mmol) in 1,2-dichloroethane (15 mL). After 30 min, the reaction was heated to 55° C. for 48 h. The reaction was quenched by the careful addition of saturated aqueous sodium bicarbonate and the mixture extracted with dichlormethane (4×). The combined organic layers were washed with 1N sodium potassium tartrate, brine, dried over MgSO₄, filtered, and concentrated. The crude product was purified by silica gel chromatography, eluting with a gradient of 50 to 100% ethyl acetate:hexanes to give the title compound (2.44 g). MS: m/z=430.0 (M+1).

Step D. Benzyl 4-[2-((3-bromopyridin-2-yl){[2-(trimethylsilyl)ethoxy]methyl}amino)-2-oxoethyl]-3,6-dihydropyridine-1(2H)-carboxylate Sodium hydride (60% dispersion in mineral oil; 117 mg, 4.88 mol) was added in portions over 10 min to a solution of benzyl 4-{2-[(3-bromopyridin-2-yl)amino]-2-oxoethyl}-3,6-dihydropyridine-1(2B)-carboxylate (1.91 g, 4.43 mol) in THF (15 mL) at 0° C. After 0.5 h, 2-(trimethylsilyl)ethoxymethyl chloride (0.861 mL, 4.88 mol) was then added slowly, keeping the temperature of the reaction mixture below 10° C. After 4 h, sodium hydride (60 mg) and 2-(trimethylsilyl)ethoxymethyl chloride (0.45 ml) were added and the reaction allowed to warm to room temperature overnight. The reaction was quenched with saturated aqueous ammonium chloride and the mixture was extracted with CH₂Cl₂ (3×). The combined organic layers were dried over MgSO₄, filtered, and concentrated. The crude product was purified by silica gel chromatography, eluting with a gradient of 40 to 70% ethyl acetate:hexanes to give the title compound (1.51 g). MS: m/z=560.2 (M+1).

Step E. Benzyl 2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate To a mixture of N-methyldicyclohexylamine (0.042 mg, 0.20 mmol) and benzyl 4-[2-((3-bromopyridin-2-yl){[2-(trimethylsilyl)ethoxy]methyl}amino)-2-oxoethyl]-3,6-dihydropyridine-1(2H)-carboxylate (100 mg, 0.178 mmol) in dioxane (2 mL) was added bis(tri-tert-butylphosphine) palladium(0) (9 mg, 0.018 mmol). After 5 min, the reaction was heated to 50° C. After 90 min, bis(tri-tert-butylphosphine) palladium(0) (9 mg) was added. After an additional 30 min at 50° C., the reaction mixture was diluted with water and extracted with ether (3×). The combined organic layers were dried over MgSO₄, filtered, and concentrated. The crude product was purified by silica gel chromatography, eluting with a gradient of 5 to 60% ethyl acetate:hexanes to give the title compound (68 mg). MS: m/z=480.2 (M+1).

Step F. 1H-Spiro[1,8-naphthyridine-4,4'-piperidin]-2(3H)-one

To a mixture of benzyl 2-oxo-1-{[2-(trimethylsilyl)ethoxy]methyl}-2,2',3,3'-tetrahydro-1H,1'H-spiro[1,8-naphthyridine-4,4'-pyridine]-1'-carboxylate (384 mg, 0.800 mmol) in dichloromethane (10 mL) was added trifluoroacetic acid (10 mL). After 3 h, the reaction was concentrated, diluted with dichloromethane (10 mL) and ethylenediamine (720 mg, 12.0 mmol) was added. After 18 h, the reaction was concentrated, the residue partitioned between saturated aqueous NaHCO₃ and dichloromethane, and the layers separated. The aqueous phase was extracted with further portions of dichloromethane (2×), the organic layers combined, dried, and concentrated. 10% Palladium on carbon (300 mg) was added to a solution of this material in EtOH (10 mL). The reaction vessel was evacuated and back-filled with nitrogen (3×), then back-filled with hydrogen (1 atm). After 24 h, the mixture was filtered though celite and concentrated to give the title compound (130 mg). MS 218.1 (M+1). ¹H NMR (500 MHz, CD₃OD) δ 8.14 (dd, J=1.6, 5.0 Hz, 1H), 7.80 (dd, J=1.6, 7.7 Hz, 1H), 7.10 (dd, J=5.0, 7.7 Hz, 1H), 2.98-2.95 (m, 4H), 2.78 (s, 2H), 1.96-1.90 (m, 2H), 1.69 (brd, J=11.5 Hz, 2H).

INTERMEDIATE 6

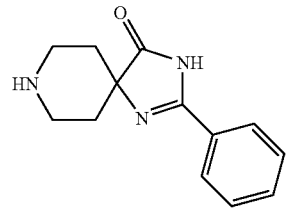

2-Phenyl-1,3,8-triazaspiro[4.5]dec-1-en-4-one

Step A. tert-Butyl 4-(aminocarbonyl)-4-{[(benzyloxy)carbonyl]amino}piperidine-1-carboxylate To a solution of 4-benzyloxycarbonylamino-piperidine-1,4-dicarboxylic acid mono-tert-butyl ester (2.09 g, 5.52 mmol) in DMF (10 mL) was added 1-[3-(dimethylamino)propyl]-3-ethylcarbodiimide hydrochloride (1.27 g, 6.63 mmol), 1-hydroxy-7-azabenzotriazole (0.373 g, 2.76 mmol) and triethylamine (0.924 mL, 6.63 mmol), followed by ammonia (0.5 M in MeOH, 13.3 mL, 6.63 mmol). After 18 h the mixture was concentrated and the residue was partitioned between saturated aqueous NaHCO₃ and ethyl acetate, the organic layer dried over MgSO₄, and concentrated. The crude product was purified by silica gel chromatography, eluting with a gradient of 0 to 6% methanol:dichloromethane to give the title compound (0.43 g). MS: m/z=378.2 (M+1).

Step B. 1 tert-butyl 4-amino-4-(aminocarbonyl)piperidine-1-carboxylate

10% Palladium on carbon (200 mg) was added to a solution of tert-Butyl 4-(aminocarbonyl)-4-{[(benzyloxy)carbonyl]amino}piperidine-1-carboxylate (430 mg, 1.14 mmol) in EtOH (20 mL). The reaction vessel was evacuated and back-filled with nitrogen (3×), then back-filled with hydrogen (1 atm). After 24 h, the mixture was filtered though celite and concentrated to give the title compound (0.29 g).

Step C. tert-butyl 4-oxo-2-phenyl-1,3,8-triazaspiro[4.5]dec-1-ene-8-carboxylate A solution of tert-butyl 4-amino-4-(aminocarbonyl)piperidine-1-carboxylate (120 mg, 0.493 mmol) and trimethyl orthobenzoate (198 mg, 1.09 mmol) in toluene (7 mL) was heated at 110° C. for 18 h. The reaction was concentrated and the crude product was purified by silica gel chromatography, eluting with a gradient of 0 to 5% methanol:dichloromethane to give the title compound (50 mg). MS: m/z=330.2 (M+1).

Step D.
2-Phenyl-1,3,8-triazaspiro[4.5]dec-1-en-4-one

To a solution of tert-butyl 4-oxo-2-phenyl-1,3,8-triazaspiro[4.5]dec-1-ene-8-carboxylate (45 mg, 0.137 mmol) in dichloromethane (5 mL) was added trifluoroacetic acid (2 mL). After 2 h the reaction was concentrated to give the title compound. MS: m/z=230.1 (M+1).

INTERMEDIATE 17

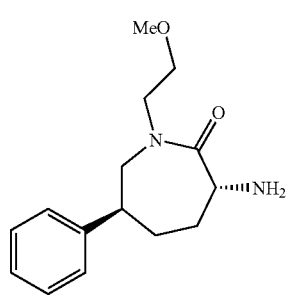

(3R,6S)-3-Amino-1-(2-methoxyethyl)-6-phenylazepan-2-one

Step A:
2-Bromo-N-(2,4-dimethoxybenzyl)prop-2-en-1-amine

Triethylamine (16.0 mL, 114 mmol) was added to a solution of 2,4-dimethoxybenzylamine hydrochloride (11.1 g, 54.5 mmol) and 2,3-dibromopropene (10.9 g, 54.5 mmol) in dichloromethane (200 mL. After 18 h, water was added and the mixture was extracted with dichloromethane (3×). The combined organic extracts were washed with saturated brine, dried over magnesium sulfate, filtered and concentrated. Purification by silica gel chromatography [100% dichloromethane→95% dichloromethane/5% (10% ammonium hydroxide/methanol)] gave the title compound (7.85 g).

Step B: Benzyl (1R)-1-{[(2-bromoprop-2-enyl)(2,4-dimethoxybenzyl)amino]carbonyl}but-3-enylcarbamate 1-[3-(Dimethylamino)propyl]-3-ethylcarbodiimide hydrochloride (55 mg, 0.285 mmol) was added to a solution of 2-bromo-N-(2,4-dimethoxybenzyl)prop-2-en-1-amine (73 mg, 0.256 mmol) and (2R)-2-{[(benzyloxy)carbonyl]amino}pent-4-enoic acid (71 mg, 0.285 mmol) in dichloromethane (5 mL). After 18 h the mixture was concentrated. Purification by silica gel chromatography (5% ethyl acetate/hexanes→30% ethyl acetate/hexanes) gave the title compound (77 mg). MS 517 (M+1).

Step C: Benzyl (1R)-1-{[(2,4-dimethoxybenzyl)(2-phenylprop-2-enyl)amino]carbonyl}but-3-enylcarbamate Tetrakis(triphenylphosphine)palladium(0) (1.11 g, 0.962 mmol) was added to a solution of benzyl (1R)-1-{[(2-bromoprop-2-enyl)(2,4-dimethoxybenzyl)amino]carbonyl}but-3-enylcarbamate (2.49 g, 4.81 mmol), phenylboronic acid (0.65 g, 5.29 mmol) and sodium carbonate (2M in water; 4.81 mL, 9.63 mmol) in tetrahydrofuran (54 mL) and water (20 mL), and the mixture heated to 60° C. After 1 h, the mixture was allowed to cool to ambient temperature and extracted with dichloromethane (3×). The combined organic extracts were washed with saturated brine, dried over magnesium sulfate, filtered and concentrated. Purification by silica gel chromatography (5% ethyl acetate/hexanes→30% ethyl acetate/hexanes) gave the title compound (2.02 g). MS 515 (M+1).

Step D: Benzyl (3R)-1-(2,4-dimethoxybenzyl)-2-oxo-6-phenyl-2,3,4,7-tetrahydro-1H-azepin-3-ylcarbamate

[1,3-bis-(2,4,6-trimethylphenyl-2-imidazolidinylidene)dichloro(phenylmethylene)-(tricyclohexylphosphine)ruthenium] (Grubbs second generation catalyst) (0.68 g, 0.79 mmol) was added to a solution of benzyl (1R)-1-{[(2,4-dimethoxybenzyl)(2-phenylprop-2-enyl)amino]carbonyl}but-3-enylcarbamate (2.02 g, 3.93 mmol) in dichloromethane (395 mL) and heated to 40° C. After 40 h, the mixture was allowed to cool to ambient temperature and concentrated. Purification by silica gel chromatography (5% ethyl acetate/hexanes→30% ethyl acetate/hexanes) gave the title compound (1.00 g). MS 487 (M+1). $^1$HNMR (500 MHz, CDCl$_3$) δ 7.39-7.31 (m, 5H), 7.26-7.19 (m, 3H), 7.17 (d, J=8.3 Hz, 1H), 6.99 (d, J=7.1 Hz, 2H), 6.41 (dd, J=8.3, 2.0 Hz, 1H), 6.33 (s, 1H), 6.22 (d, J=6.4 Hz, 1H), 5.77-5.76 (m, 1H), 5.16-5.09 (m, 3H), 4.82 (d, J=14.7 Hz, 1H), 4.65 (dd, J=17.6, 2.7 Hz, 1H), 4.54 (d, J=14.4 Hz, 1H), 3.93 (d, J=17.6 Hz, 1H), 3.77 (s, 3H), 3.64 (s, 3H), 2.91-2.86 (m, 1H), 2.42-2.36 (m, 1H).

Step E: Benzyl (3R)-2-oxo-6-phenyl-2,3,4,7-tetrahydro-1H-azepin-3-ylcarbamate A solution of L-methionine (2.56 g, 17.2 mmol) in trifluoroacetic acid (15 mL) was added to a solution of benzyl (3R)-1-(2,4-dimethoxybenzyl)-2-oxo-6-phenyl-2,3,4,7-tetrahydro-1H-azepin-3-ylcarbamate (0.84 g, 1.72 mmol) in dichloromethane (20 mL). After 18 h, the mixture was concentrated and water was added. The mixture was extracted with ethyl acetate, washed with water (2×), saturated aqueous sodium bicarbonate (2×), saturated brine, dried over magnesium sulfate, filtered and concentrated. Purification by silica gel chromatography (5% ethyl acetate/hexanes→50% ethyl acetate/hexanes) gave the title compound (0.44 g). MS 337 (M+1).

Step F: tert-Butyl (3R,6S)-2-oxo-6-phenylazepan-3-ylcarbamate

10% Palladium on carbon (75 mg) was added to a solution of benzyl (3R)-2-oxo-6-phenyl-2,3,4,7-tetrahydro-1H-azepin-3-ylcarbamate (596 mg, 1.77 mmol) and di-tert-butyl dicarbonate (773 mg, 3.54 mmol) in ethyl acetate (30 mL). The reaction vessel is evacuated and back-filled with nitrogen (3×), then back-filled with hydrogen (1 atm). After 2 h, the mixture was filtered and concentrated. Purification by silica gel chromatography (30% ethyl acetate/hexanes→50% ethyl acetate/hexanes) gave the title compound (289 mg).

Step G: tert-Butyl (3R,6S)-1-(2-methoxyethyl)-2-oxo-6-phenylazepan-3-ylcarbamate Sodium hydride (60% dispersion in mineral oil; 6.2 mg, 0.158 mmol) was added to a solution of tert-butyl (3R,6R)-2-oxo-6-phenylazepan-3-ylcarbamate (40 mg, 0.131 mmol) and 2-bromoethyl methyl ether (0.013 mL, 0.138 mmol) in N,N-dimethylformamide (2 mL) at 0° C. After addition, the mixture was allowed to warm to ambient temperature. After 4 h, the reaction was quenched with water and the mixture was extracted with ethyl acetate. The organic layer was washed with water (3×), saturated brine, dried over magnesium sulfate, filtered and concentrated. Purification by silica gel chromatography (5% ethyl acetate/hexanes→30% ethyl acetate/hexanes) gave the title compound (41 mg). MS 363 (M+1).

Step H: (3R,6L)-3-Amino-1-(2-methoxyethyl)-6-phenylazepan-2-one

Trifluoroacetic acid (2.5 mL) was added to a solution of tert-butyl (3R,6S)-1-(2-methoxyethyl)-2-oxo-6-phenylazepan-3-ylcarbamate (41 mg, 0.113 mmol) in dichloromethane (5 mL). After 1 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated. MS 263 (M+1). $^1$H NMR (500 MHz, CDCl$_3$) δ 7.32 (t, J=7.3 Hz, 2H), 7.25-7.22 (m, 1H), 7.18 (d, J=8.3 Hz, 2H), 3.83-3.76 (m, 3H), 3.56-3.49 (m, 3H), 3.35 (s, 3H), 3.34-3.30 (m, 1H), 2.77-2.72 (m, 1H), 2.13-2.10 (m, 1H), 2.03-1.94 (m, 2H), 1.74-1.68 (m, 1H).

INTERMEDIATE 8

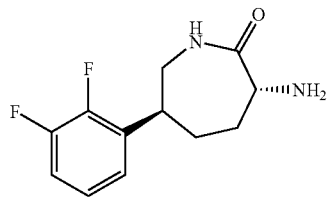

(3R,6S)-3-Amino-6-(2,3-difluorophenyl)azepan-2-one

Step A.
2-Bromo-N-(2,4-dimethoxybenzyl)prop-2-en-1-amine

Triethylamine (16.0 mL, 114 mmol) was added to a solution of 2,4-dimethoxybenzylamine hydrochloride (11.1 g, 54.5 mmol) and 2,3-dibromopropene (10.9 g, 54.5 mmol) in dichloromethane (200 mL). After 18 h, water was added and the mixture was extracted with dichloromethane (3×). The combined organic extracts were washed with saturated brine, dried over magnesium sulfate, filtered and concentrated. Purification by silica gel chromatography [100% dichloromethane→95% dichloromethane/5% (10% ammonium hydroxide/methanol)] gave the title compound (7.85 g).

Step B. Benzyl (1R)-1-{[(2-bromoprop-2-enyl)(2,4-dimethoxybenzyl)amino]carbonyl}but-3-enylcarbamate 1-[3-(Dimethylamino)propyl]-3-ethylcarbodiimide hydrochloride (55 mg, 0.285 mmol) was added to a solution of 2-bromo-N-(2,4-dimethoxybenzyl)prop-2-en-1-amine (73 mg, 0.256 mmol) and (2R)-2-{[(benzyloxy)carbonyl]amino}pent-4-enoic acid (71 mg, 0.285 mmol) in dichloromethane (5 mL). After 18 h the mixture was concentrated. Purification by silica gel chromatography (5% ethyl acetate/hexanes→30% ethyl acetate/hexanes) gave the title compound (77 mg). MS 517 (M+1).

Step C. Benzyl (1R)-1-{[[2-(2,3-difluorophenyl)prop-2-enyl](2,4-dimethoxybenzyl)amino]carbonyl}but-3-enylcarbamate Dichloro[1,1'-bis(diphenylphosphino)ferrocene]palladium dichloromethane adduct (0.726 g, 0.889 mmol) was added to a solution of benzyl (1R)-1-{[(2-bromoprop-2-enyl)(2,4-dimethoxybenzyl)amino]carbonyl}but-3-enylcarbamate (9.2 g, 17.8 mmol), 2,3-difluorophenylboronic acid (2.95 g, 18.7 mmol) and sodium carbonate (2M in water; 19.6 mL, 39.1 mmol) in N,N-dimethylformamide (60 mL) and the mixture was heated to 75° C. After 2 h, the mixture was allowed to cool to ambient temperature and extracted with dichloromethane (3×). The combined organic extracts were washed with saturated brine, dried over magnesium sulfate, filtered and concentrated. Purification by silica gel chromatography (5% ethyl acetate/hexanes→55% ethyl acetate/hexanes) gave the title compound (6.8 g). MS 551.2 (M+1).

Step D. Benzyl (3R)-6-(2,3-difluorophenyl)-1-(2,4-dimethoxybenzyl)-2-oxo-2,3,4,7-tetrahydro-1H-azepin-3-ylcarbamate

[1,3-bis-(2,4,6-Trimethylphenyl-2-imidazolidinylidene)dichloro(phenylmethylene)-(tricyclohexylphosphine)ruthenium] (Grubbs second generation catalyst) (2.62 g, 3.09 mmol) was added to a solution of benzyl (1R)-1-{[[2-(2,3-difluorophenyl)prop-2-enyl](2,4-dimethoxybenzyl)amino]carbonyl}but-3-enylcarbamate (6.8 g, 12.35 mmol) in dichloromethane (1800 mL) and the solution was heated to 40° C. After 48 h, additional catalyst was added (0.52 g, 0.61 mmol) and the reaction continued to heat at 40° C. for an additional 48 h. The mixture was allowed to cool to ambient temperature and concentrated. Purification by silica gel chromatography (5% ethyl acetate/hexanes →55% ethyl acetate/hexanes) gave the title compound (3.71 g). MS 523.1 (M+1).

Step E. Benzyl (3R)-6-(2,3-difluorophenyl)-2-oxo-2,3,4,7-tetrahydro-1H-azepin-3-ylcarbamate Trifluoroacetic acid (60 mL) was added to a solution of benzyl (3R)-6-(2,3-difluorophenyl)-1-(2,4-dimethoxybenzyl)-2-oxo-2,3,4,7-tetrahydro-1H-azepin-3-ylcarbamate (3.70 g, 7.08 mmol) in dichloromethane (40 mL). After 18 h, the mixture was concentrated at 25° C., methanol (150 mL) was added, and the precipitate filtered. The filtrate was concentrated, diluted with dichloromethane (100 mL), washed with water (2×), saturated aqueous sodium bicarbonate (2×), saturated brine, dried over magnesium sulfate, filtered and concentrated. Purification by silica gel chromatography (5% ethyl acetate/hexanes→65% ethyl acetate/hexanes) gave the title compound (1.75 g). MS 373.1 (M+1).

Step F. tert-Butyl (3R,6S)-6-(2,3-difluorophenyl)-2-oxoazepan-3-ylcarbamate

10% Palladium on carbon (700 mg) was added to a solution of benzyl (3R)-6-(2,3-difluorophenyl)-2-oxo-2,3,4,7-tetrahydro-1H-azepin-3-ylcarbamate (2.6 g, 6.98 mmol) and di-tert-butyl dicarbonate (5.03 g, 23.0 mmol) in toluene (200 mL). The reaction vessel was evacuated and back-filled with nitrogen (3×), then back-filled with hydrogen (1 atm). After 24 h, the mixture was filtered and concentrated. Purification by preparative reverse phase chromatography (DeltaPak C18, 15μ, 47 mm×300 mm, 70 mL/min:80% H$_2$O/NH$_4$OAc:20% CH$_3$CN to 100% CH$_3$CN over 60 min) afforded the pure trans title compound (1.2 g). MS 341.2 (M+1). $^1$HNMR (500 MHz, CDCl$_3$) δ 7.07-7.04 (m, 2H), 6.91-6.89 (m, 1H), 6.04 (br s, 1H), 5.93 (d, J=5.6 Hz, 1H), 4.46 (dd, J=10.5, 4.6 Hz, 1H), 3.65-3.59 (m, 1H), 3.21 (dd, J=15.1, 7.3 Hz, 1H), 3.05-3.00 (m, 1H), 2.25-2.20 (m, 1H), 2.17-2.10 (m, 2H), 1.79-1.71 (m, 1H), 1.46 (s, 9H).

Step G. (3R,6S)-3-Amino-6-(2,3-difluorophenyl) azepan-2-one

Trifluoroacetic acid (4 mL) was added to a solution of tert-butyl (3R,6S)-6-(2,3-difluorophenyl)-2-oxoazepan-3-ylcarbamate (82 mg, 0.241 mmol) in dichloromethane (4 mL). After 1 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated. MS 241.0 (M+1)

Alternatively, Intermediate 68 can be made in the following manner:

Step H. 1-Benzyl 5-methyl N,N-bis(tert-butoxycarbonyl-D-glutamate

To a solution of Boc-D-Glu-OBn (50.0 g, 148.2 mmol) in DCM (400 ml) and MeOH (100 ml) was added trimethylsilyldiazomethane (88.9 mL of 2.0 M solution in hexanes, 117.8 mmol) at 0° C. dropwise via an addition funnel. After 60 min the reaction was concentrated. This residue was diluted with CH$_3$CN (400 mL) and (Boc)$_2$O (48.5 g, 222.3 mmol) was added followed by DMAP (18.1 g, 14.8 mmol). After 24 h the reaction was concentrated and purified by silica gel chromatography (10%→60% ethyl acetate/hexanes) to give the title compound (48.20 g, 72%). MS 252.2 (M+1−2Boc).

Step I. Benzyl (2R,5E)-2-[bis(tert-butoxycarbonyl) amino]-6-nitrohex-5-enoate

To a −78° C. of 1-benzyl 5-methyl N,N-bis(tert-butoxycarbonyl)-D-glutamate (48.2 g, 106.8 mmol) in Et$_2$O (400 mL), was added DIBAL (133.4 mL of 1.0 M solution in toluene, 133.4 mmol) slowly so as not to let the internal temperature exceed −65° C. After 15 min, 20 mL more of DIBAL was added. After stirring for additional 20 min, water (300 mL) was added and the reaction was warmed to room temperature and stirred for 30 min. This mixture was further diluted with Et$_2$O and H$_2$O, the layers separated and the aqueous phase extracted with more Et$_2$O. The combined organics extracts were washed with a saturated aqueous solution of sodium potassium tartrate (2×), brine, dried over magnesium sulfate, filtered and concentrated to give benzyl N,N-bis(tert-butoxycarbonyl)-5-oxo-D-norvalinate (44.4 g) which was carried directly into the next step. MS 444.1 (M+Na). This material was dissolved in toluene (310 mL) and nitromethane (57.1 mL, 1.05 mol) and 1,1,3,3-tetramethylguanidine (1.3 mL, 10.5 mmol) were added at 0° C. After stirring for 30 min the nitroaldol reaction was complete, so methanesulfonyl chloride (12.2 mL, 158 mmol) was added followed triethylamine (22.0 mL, 158 mmol) at 0° C. and the reaction was allowed to warm to RT. After 1 h, 4 mL MsCl and 5.5 mL triethylamine were added. After stirring for an additional 30 min the mixture was diluted with Et$_2$O and NaHCO$_3$, the phases separated and the aqueous layer backwashed with another portion of Et$_2$O. The combined organics were dried over magnesium sulfate, filtered and concentrated to give a residue that was purified by silica gel chromatography (5%→50% ethyl acetate/hexanes) to give the title compound (34.3 g, 70%). MS 487.1 (M+Na).

Step J. Benzyl (5S)—N,N-bis(tert-butoxycarbonyl)-5-(2,3-difluorophenyl)-6-nitro-D-norleucinate A solution of benzyl (2R,5E)-2-[bis(tert-butoxycarbonyl) amino]-6-nitrohex-5-enoate (34.0 g, 73.2 mmol), 2,3-difluorophenylboronic acid (28.9 g, 183.0 mmol) and water (4.62 mL, 256.2 mmol) in dioxane (240 mL) was degassed with argon for 15 min. To this solution was added sodium bicarbonate (3.08 g, 36.6 mmol), (S)-BINAP (1.28 g, 2.05 mmol) and acetylacetanotobis(ethylene)rhodium(I) (0.472 g, 1.83 mmol). The mixture was stirred at RT for 2 min then heated to 35° C. After 4 h, 255 mg of (S)-BINAP and 94 mg of acetylacetanotobis(ethylene)rhodium(I) were added. After an additional 2 h the reaction was diluted with DCM/NaHCO$_3$, the layers separated and the aqueous phase was backwashed with another portion of DCM. The combined organics were dried over magnesium sulfate, filtered and concentrated to give a residue that was purified by silica gel chromatography (5%→60% ethyl acetate/hexanes) to give the title compound (37.0 g, 87%) contaminated with ~5% 5R isomer. MS 379.1 (M+1−2Boc).

Step K. (5S)—N$^2$,N$^2$-Bis(tert-butoxycarbonyl)-5-(2,3-difluorophenyl)-D-lysine A solution of benzyl (5S)—N,N-bis(tert-butoxycarbonyl)-5-(2,3-difluorophenyl)-6-nitro-D-norleucinate (15.5 g, 26.8 mmol) and 10% Pd/C (12.0 g) in EtOH (175 mL, SureSeal from Aldrich), was hydrogenated at 55 psi overnight. After 18 h, another 4 g of 10% Pd/C was added and the reaction hydrogenated at 55 psi for another 18 h. The reaction was filtered through Celite with more EtOH and concentrated to afford the title compound (12.0 g). MS 459.2 (M+1).

Step L. tert-Butyl (3R,6S)-6-(2,3-difluorophenyl)-2-oxoazepan-3-ylcarbamate

To a solution (5S)—N$^2$,N$^2$-bis(tert-butoxycarbonyl)-5-(2,3-difluorophenyl)-D-lysine (22.0 g, 48.0 mmol) in DCM (700 mL) were added EDC (11.0 g, 57.6 mmol) and HOAT (3.27 g, 24.0 mmol) followed by triethylamine (10.0 mL, 72.0 mmol). After 60 min, NaHCO$_3$ was added, the layers separated and the aqueous phase backwashed with DCM. The combined organics were dried over magnesium sulfate, filtered and concentrated. The residue was purified by silica gel chromatography (10% MeOH/DCM) to give the cyclized compound (18.0 g). A portion of this material (2.60 g, 5.90 mmol) was diluted DCM (60 mL) and TFA (1.20 mL, 11.8 mmol) was added. After 1 h, NaHCO$_3$ was added, the layers separated and the aqueous phase backwashed with DCM. The combined organics were dried over magnesium sulfate, filtered and concentrated and the residue purified by silica gel chromatography (5%→50% EtOAc/DCM) to give the title compound (1.14 g). MS 341.1 (M+1).

INTERMEDIATE 9

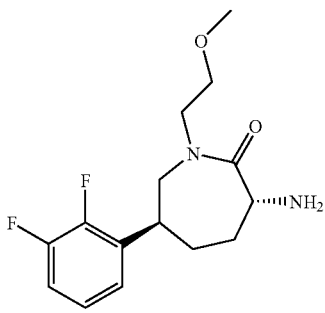

(3R,6S)-3-Amino-6-(2,3-difluorophenyl)-1-(2-methoxyethyl)azepan-2-one

Step A. tert-Butyl (3R,6S)-6-(2,3-difluorophenyl)-1-(2-methoxyethyl)-2-oxoazepan-3-ylcarbamate Sodium hydride (60% dispersion in mineral oil; 17.6 mg, 0.264 mmol) was added to a solution of tert-butyl (3R,6S)-6-(2,3-difluorophenyl)-2-oxoazepan-3-ylcarbamate (75 mg, 0.220 mmol) in N,N-dimethyl formamide (2 mL) at 0° C. After 5 min, 2-bromoethyl methyl ether (0.025 mL, 0.264 mmol) was added and the mixture was allowed to warm to ambient temperature. After 3 h, the reaction was quenched with water and the mixture was extracted with ethyl acetate. The organic layer was washed with water (2×), saturated brine, dried over magnesium sulfate, filtered and concentrated to give the title compound. MS 421 (M+Na).

Step B. (3R,6S)-3-Amino-6-(2,3-difluorophenyl)-1-(2-methoxyethyl)azepan-2-one Trifluoroacetic acid (2.5 mL) was added to a solution of tert-butyl (3R,6S)-6-(2,3-difluorophenyl)-1-(2-methoxyethyl)-2-oxoazepan-3-ylcarbamate (99 mg, 0.248 mmol) in dichloromethane (5 mL). After 1 h, the solution was concentrated and azeotroped with toluene (2×). Saturated aqueous sodium bicarbonate solution was added and the mixture was extracted with dichloromethane (3×). The combined organic extracts were washed with saturated brine, dried over magnesium sulfate, filtered and concentrated. MS 299.2 (M+1).

INTERMEDIATE 10

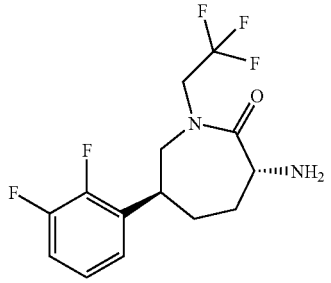

(3R,6S)-3-Amino-6-(2,3-difluorophenyl)-1-(2,2,2-trifluoroethyl)azepan-2-one

Step A: tert-Butyl (3R,6S)-6-(2,3-difluorophenyl)-2-oxo-1-(2,2,2-trifluoroethyl)azepan-3-ylcarbamate Sodium hydride (60% dispersion in mineral oil; 70.7 mg, 1.06 mmol) was added to a solution of tert-butyl (3R,6S)-6-(2,3-difluorophenyl)-2-oxoazepan-3-ylcarbamate (301 mg, 0.884 mmol) in N,N-dimethylformamide (7 mL) at −35° C. After 15 min, 2,2,2-trifluoroethyl trichloromethanesulfonate (0.314 mL, 1.91 mmol) was added and the reaction was stirred at −35° C. After 30 min, an additional amount of sodium hydride (27 mg, 0.40 mmol) and 2,2,2-trifluoroethyl trichloromethanesulfonate (0.140 mL, 0.85 mmol) were added. After 2 h, the reaction was quenched with water and the mixture was extracted with ethyl acetate. The organic layer was washed with water (3×), saturated brine, dried over magnesium sulfate, filtered and concentrated. Purification by silica gel chromatography (0% ethyl acetate/hexanes→30% ethyl acetate/hexanes) gave the title compound (306 mg). MS 423 (M+1).

Step B: (3R,6S)-3-Amino-6-(2,3-difluorophenyl)-1-(2,2,2-trifluoroethyl)azepan-2-one Trifluoroacetic acid (2.5 mL) was added to a solution of tert-butyl (3R,6S)-6-(2,3-difluorophenyl)-2-oxo-1-(2,2,2-trifluoroethyl)azepan-3-ylcarbamate (135 mg, 0.320 mmol) in dichloromethane (5 mL). After 30 min, the solution was concentrated and azeotroped with toluene (2×). Saturated aqueous sodium bicarbonate solution was added and the mixture was extracted with dichloromethane (3×). The combined organic extracts were washed with saturated brine, dried over magnesium sulfate, filtered and concentrated. MS 323.1 (M+1). $^1$H NMR (500 MHz, CDCl$_3$) δ 7.11-7.03 (m, 2H), 6.93-6.89 (m, 1H), 4.21-4.13 (m, 1H), 4.10-3.98 (m, 2H), 3.85 (d, J=11.0 Hz, 1H), 3.35 (d, J=15.4 Hz, 1H), 3.04-2.99 (m, 1H), 2.13-2.09 (m, 2H), 2.08-2.02 (m, 1H), 1.78-1.70 (m, 3H).

INTERMEDIATE 11

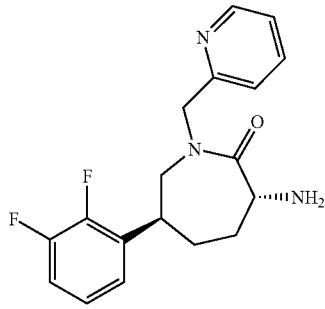

(3R,6S)-3-Amino-6-(2,3-difluorophenyl)-1-(pyridin-2-ylmethyl)azepan-2-one

Step A. tert-Butyl (3R,6S)-6-(2,3-difluorophenyl)-2-oxo-1-(pyridin-2-ylmethyl)azepan-3-ylcarbamate Sodium hydride (60% dispersion in mineral oil; 30 mg, 1.175 mmol) was added to a solution of tert-butyl (3R,6S)-6-(2,3-difluorophenyl)-2-oxoazepan-3-ylcarbamate (160 mg, 0.470 mmol) in N,N-dimethylformamide (6 mL) at 0° C. After 30 min, 2-bromomethylpyridine (0.125 mg, 0.494 mmol) was added. After 1 h, the reaction was quenched with water and the mixture was extracted with ethyl acetate. The organic layer was washed with water (2×), saturated brine, dried over magnesium sulfate, filtered and concentrated to give the title compound (202 mg). MS 432.2 (M+1).

Step B. (3R,6S)-3-Amino-6-(2,3-difluorophenyl)-1-(pyridin-2-ylmethyl)azepan-2-on Trifluoroacetic acid (3 mL) was added to a solution of tert-butyl (3R,6S)-6-(2,3-difluorophenyl)-2-oxo-1-(pyridin-2-ylmethyl)azepan-3-ylcarbamate (202 mg, 0.468 mmol) in dichloromethane (4 mL). After 18 h, the solution was concentrated. Saturated aqueous sodium bicarbonate solution was added and the mixture was extracted with dichloromethane (3×). The combined organic extracts were washed with saturated brine, dried over magnesium sulfate, filtered and concentrated. MS 332.2 (M+1).

INTERMEDIATE 12

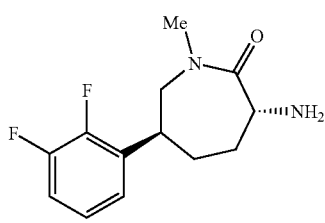

(3R,6S)-3-amino-6-(2,3-difluorophenyl)-1-methylazepan-2-one

This intermediate was prepared essentially following the procedures outlined for the preparation of Intermediates 9-11. MS 255.2 (M+1).

INTERMEDIATE 13

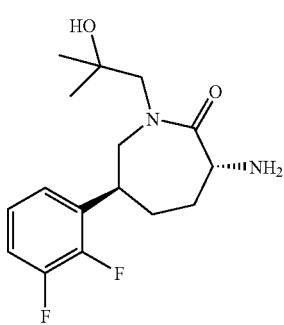

(3R,6S)-3-Amino-6-(2,3-difluorophenyl)-1-(2-hydroxy-2-methylpropyl)azepan-2-one

Step A. Di-tert-butyl[(3R,6S)-6-(2,3-difluorophenyl)-1-(2-hydroxy-2-methylpropyl)-2-oxoazepan-3-yl]imidodicarbonate A solution of (5S)—$N^2,N^2$-bis(tert-butoxycarbonyl)-5-(2,3-difluorophenyl)-D-lysine (0.569 g, 1.24 mmol), 1-chloro-2-methyl-2-propanol (0.202 g, 1.86 mmol) and diisopropylethylamine (0.529 g, 4.10 mmol) in EtOH (5 mL) was heated at 75° C. overnight. The reaction was concentrated to dryness, diluted with DCM (20 mL) and EDC (0.358 g, 1.87 mmol), HOAT (0.252 g, 1.87 mmol) were added followed by diisopropylethylamine (0.650 mL, 3.73 mmol). After stirring overnight, NaHCO₃ was added, the layers separated and the aqueous phase backwashed with DCM. The combined organics were dried over magnesium sulfate, filtered, concentrated and the residue purified by silica gel chromatography (10%→35% EtOAc/hexanes) to give the title compound (0.21 g). MS 513.1 (M+1). ¹H NMR (500 MHz, CD₃OD) δ 7.1 (m, 3H), 5.24 (d, J=10.7 Hz, 1H), 4.02 (m, 1H), 3.69 (d, J=13.9 Hz, 1H), 3.60 (d, J=15.1 Hz, 1H), 3.39 (m, 1H), 3.24 (d, J=14.2 Hz, 1H), 2.4 (m, 1H), 2.1 (m, 3H), 1.5 (s, 18H), 1.20 (s, 3H), 1.16 (s, 3H).

Step B. (3R,6S)-3-Amino-6-(2,3-difluorophenyl)-1-(2-hydroxy-2-methylpropyl)azepan-2-one A solution of di-tert-butyl[(3R,6S)-6-(2,3-difluorophenyl)-1-(2-hydroxy-2-methylpropyl)-2-oxoazepan-3-yl]imidodicarbonate (0.095 g, 0.185 mmol) in DCM (10 mL) was treated with trifluoroacetic acid (3 mL). After 1 h the reaction was concentrated to dryness to afford the title compound as a TFA salt. MS 313.2 (M+1).

INTERMEDIATE 14

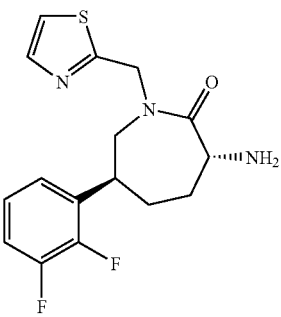

(3R,6S)-3-Amino-6-(2,3-difluorophenyl)-1-(1,3-thiazol-2-ylmethyl)azepan-2-one

Step A. Di-tert-butyl[(3R,6S)-6-(2,3-difluorophenyl)-2-oxo-1-(1,3-thiazol-2-ylmethyl)azepan-3-yl] imidodicarbonate A solution of (5S)—$N^2,N^2$-bis(tert-butoxycarbonyl)-5-(2,3-difluorophenyl)-D-lysine (0.871 g, 1.90 mmol), 2-formylthiazole (0.183 g, 1.62 mmol) and acetic acid (0.137 g, 2.28 mmol) in 1,2-dichloroethane (20 mL) was stirred at room temperature for 30 min. Sodium triacetoxyborohydride (0.604 g, 2.85 mmol) was added and the reaction stirred overnight. The reaction was diluted with saturated aqueous sodium bicarbonate, the layers separated, and the aqueous phase extracted with DCM (2×). The organic washes were combined, dried over magnesium sulfate, and concentrated. This residue was diluted with dichloromethane (20 mL) and EDC (0.569 g, 2.97 mmol), HOAT (0.401 g, 2.97 mmol) were added followed by diisopropylethylamine (1.04 mL, 5.94 mmol). After stirring overnight, NaHCO₃ was added, the layers separated and the aqueous phase backwashed with DCM. The combined organics were dried over magnesium sulfate, filtered, concentrated and the residue purified by silica gel chromatography (0%→40% EtOAc/hexanes) to give the title compound (0.49 g). MS 538.0 (M+1). ¹H NMR (500 MHz, CDCl₃) δ 7.73 (d, J=3.5 Hz, 1H), 7.37 (d, J=3.4 Hz, 1H), 7.0 (m, 2H), 6.8 (m, 1H), 5.20 (d, J=10.3 Hz, 1H), 5.03 (d, J=15.5 Hz, 1H), 4.96 (d, J=15.5 Hz, 1H), 3.84 (dd, J=10.3, 15.2 Hz, 1H), 3.48 (d, J=15.5 Hz, 1H), 2.94 (dd, J=11.0, 11.0 Hz, 1H), 2.50 (dd, 1H), 2.0 (m, 4H), 1.5 (s, 18H).

Step B. (3R,6S)-3-Amino-6-(2,3-difluorophenyl)-1-(1,3-thiazol-2-ylmethyl)azepan-2-one A solution of di-tert-butyl[(3R,6S)-6-(2,3-difluorophenyl)-2-oxo-1-(1,3-thiazol-2-ylmethyl)azepan-3-yl]imidodicarbonate (0.481 g, 0.895 mmol) in DCM (10 mL) was treated with trifluoroacetic acid (3 mL). After 1 h the reaction was diluted with saturated aqueous sodium bicarbonate, the layers separated, and the aqueous phase extracted with DCM (2×). The organic washes were combined, dried over magnesium sulfate, and concentrated to afford the title compound (0.30 mg). MS 338.2 (M+1).

INTERMEDIATE 15

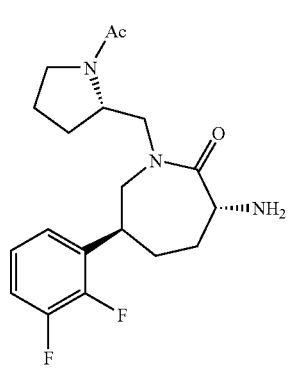

(3R,6S)-1-{[(2S)-1-acetylpyrrolidin-2-yl]methyl}-3-amino-6-(2,3-difluorophenyl)azepan-2-one This intermediate was prepared essentially following the procedures outlined for the preparation of Intermediates 13-14. MS 336.0 (M+1).

Example 1

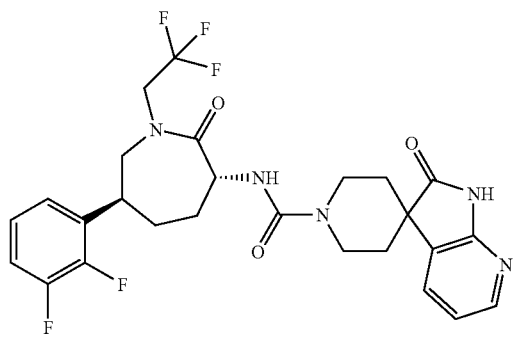

N-[(3R,6S)-6-(2,3-difluorophenyl)-2-oxo-1-(2,2,2-trifluoroethyl)azepan-3-yl]-2'-oxo-1' 2'-dihydro-1H-spiro[piperidine-4,3'-pyrrolo[2,3-b]pyridine]-1-carboxamide Triethylamine (0.025 mL, 0.179 mmol) was added to a solution of (3R,6S)-3-amino-6-(2,3-difluorophenyl)-1-(2,2,2-trifluoroethyl)azepan-2-one (48 mg, 0.149 mmol) and 4-nitrophenyl chloroformate (30 mg, 0.149 mmol) in tetrahydrofuran (5 mL) at 0° C. After 60 min, spiro[piperidine-4,3'-pyrrolo[2,3-b]pyridin]-2'(1'B)-one dihydrochloride (33 mg, 0.164 mmol), triethylamine (0.152 mL, 1.1 mmol), and chloroform (5 mL) were added and the mixture allowed to warm to ambient temperature. The reaction was stirred overnight, concentrated, diluted with saturated aqueous sodium bicarbonate and extracted with dichloromethane (2×). The organic layer was washed with water, saturated brine, dried over magnesium sulfate, filtered and concentrated. Purification by silica gel chromatography [100% dichloromethane→91% dichloromethane/methanol] gave the title compound (65 mg). MS 562.2060 (M+1). $^1$HNMR (500 MHz, CDCl$_3$) δ 10.15 (brs, 1H), 8.19 (dd, J=5.4 Hz, 1.5 Hz, 1H), 7.55 (dd, J=7.3 Hz, 1.4 Hz, 1H), 7.11-7.08 (m, 2H), 7.00-6.94 (m, 2H), 6.13 (d, J=5.3 Hz, 1H), 4.90 (dd, J=11.0, 4.9 Hz, 1H), 4.2 (m, 2H), 4.0 (m, 2H), 3.93 (m, 2H), 3.75 (m, 2H), 3.37 (d, J=15.4 Hz, 1H), 3.09 (dd, 1H), 2.32-1.73 (m, 8H).

Example 2

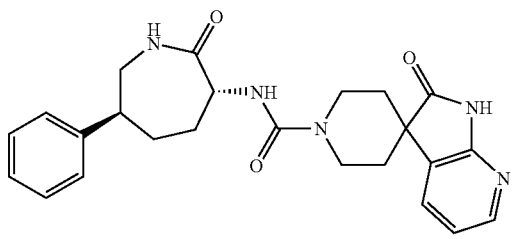

2'-oxo-N-[(3R,6S)-2-oxo-6-phenylazepan-3-yl]-1',2'-dihydro-1H-spiro[piperidine-4-3'-pyrrolo[2,3-b]pyridine]-1-carboxamide Prepared essentially following the procedure for Example 1. MS 434.2202 (M+1).

Essentially following the procedure outlined for the preparation of Example 1, the Examples in Table E-1 were prepared.

TABLE E-1

| Example | R | MS (M + 1) |
|---|---|---|
| 3 | H | 470.1990 |
| 4 | CH$_3$ | 484.2163 |
| 5 | CH$_2$CH$_2$OCH$_3$ | 528.2404 |
| 6 | CH$_2$C(CH$_3$)$_2$OH | 542.2592 |
| 7 | thiazol-2-ylmethyl (CH$_2$) | 567.1989 |
| 8 | pyridin-2-ylmethyl (CH$_2$) | 561.2415 |

TABLE E-1-continued

| Example | R | MS (M + 1) |
|---------|---|------------|
| 9 | Ac-N-pyrrolidine-CH₂ | 595.2818 |

Example 10

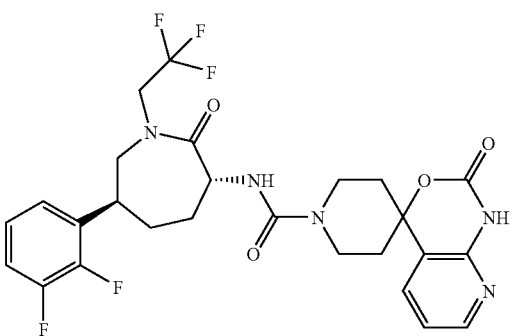

N-[(3R,6S)-6-(2,3-difluorophenyl)-2-oxo-1-(2,2,2-trifluoroethyl)azepan-3-yl]-2-oxo-1,2-dihydro-1'H-spiro[3,1-benzoxazine-4,4'-piperidine]-1'-carboxamide Triethylamine (0.027 mL, 0.192 mmol) was added to a solution of (3R,6S)-3-amino-6-(2,3-difluorophenyl)-1-(2,2,2-trifluoroethyl)azepan-2-one (62 mg, 0.192 mmol) and 4-nitrophenyl chloroformate (39 mg, 0.192 mmol) in tetrahydrofuran (3 mL) at 0° C. After 60 min, spiro[piperidine-4,4'-pyrido[2,3-d][1,3]oxazin]-2'(1'B)-one (33 mg, 0.164 mmol), triethylamine (0.054 mL, 0.38 mmol), and chloroform (3 mL) were added and the mixture allowed to warm to ambient temperature. The reaction was stirred overnight, concentrated, diluted with saturated aqueous sodium bicarbonate and extracted with dichloromethane (2×). The organic layer was washed with water, saturated brine, dried over magnesium sulfate, filtered and concentrated. Purification by silica gel chromatography [100% dichloromethane→91% dichloromethane/methanol] gave the title compound (55 mg). MS 568.2023 (M+1). $^1$H NMR (500 MHz, CDCl$_3$) δ 8.26 (dd, J=5.0 Hz, 1.5 Hz, 1H), 7.95 (brs, 1H), 7.43 (d, J=7.3 Hz, 1H), 7.08 (m, 3H), 6.95 (m, 1H), 6.07 (d, J=5.4 Hz, 1H), 4.82 (dd, J=10.6, 5.0 Hz, 1H), 4.4 (m, 1H), 4.0 (m, 4H), 3.45 (appq, 2H), 3.36 (d, J=15.6 Hz, 1H), 3.05 (dd, J=10, 10 Hz, 1H), 2.3-1.7 (m, 8H).

Essentially following the procedure outlined for the preparation of Example 10, the Examples in Table E-2 were prepared.

TABLE E-2

| Example | R | X | MS (M + 1) |
|---------|---|---|------------|
| 11 | CH₂CH₂OCH₃ | spiro[piperidine-indolin-2-one] | 527.2497 |

TABLE E-2-continued

| Example | R | X | MS (M + 1) |
|---|---|---|---|
| 12 | CH₂CF₃ | (spiro piperidine-imidazolone with 2-phenyl) | 578.2202 |
| 13 | CH₂CF₃ | (spiro piperidine-pyrrolidinone with phenyl) | 579.2408 |
| 14 | CH₂CF₃ | (spiro piperidine-dihydroquinolinone) | 565.2257 |
| 15 | CH₂CF₃ | (spiro piperidine-benzoxazinone) | 567.2024 |
| 16 | CH₂CF₃ | (spiro piperidine-naphthyridinone) | 589.2 |
| 17 | CH₂CF₃ | (spiro piperidine-hydantoin) | 518.1813 |

TABLE E-2-continued

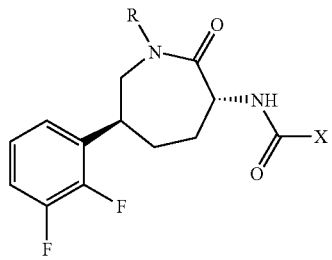

| Example | R | X | MS (M + 1) |
|---|---|---|---|
| 18 | thiazol-2-yl-CH₂ | [spiro piperidine/pyrido oxazinone] | 583.1905 |
| 19 | CH₂CF₃ | [spiro piperidine/pyrrolidinedione] | 517.2 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

The invention claimed is:

1. A compound of the Formula I:

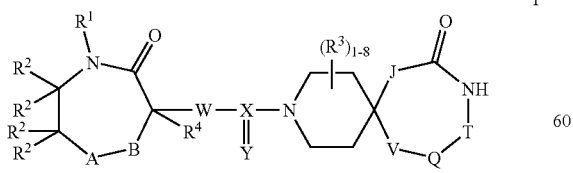

wherein:
A is C(R²)₂;
B is (C(R²)₂)ₙ wherein n is 1;
R¹ is selected from:

1) H, $C_1$-$C_6$ alkyl, $C_2$-$C_6$ alkenyl, $C_2$-$C_6$ alkynyl, $C_{3-6}$ cycloalkyl, and heterocycle, unsubstituted or substituted with one or more substituents each independently selected from:
  a) $C_{1-6}$ alkyl,
  b) $C_{3-6}$ cycloalkyl,
  c) aryl, unsubstituted or substituted with 1-5 substituents each ndependently selected from R⁴,
  d) heteroaryl, unsubstituted or substituted with 1-5 substituents each independently selected from R⁴,
  e) heterocycle, unsubstituted or substituted with 1-5 substituents each independently selected from R⁴,
  f) $(F)_p C_{1-3}$ alkyl,
  g) halogen,
  h) OR⁴,
  i) $O(CH_2)_s OR^4$,
  j) $CO_2 R^4$,
  k) (CO)NR¹⁰R¹¹,
  l) O(CO)NR¹⁰R¹¹,
  m) N(R⁴)(CO)NR¹⁰R¹¹,
  n) N(R¹⁰)(CO)R¹¹,
  o) N(R¹⁰)(CO)OR¹¹,
  p) SO₂NR¹⁰R¹¹,
  q) N(R¹⁰)SO₂R¹¹,
  r) $S(O)_m R^{10}$,
  s) CN,
  t) NR¹⁰R¹¹,
  u) N(R¹⁰)(CO)NR⁴R¹¹, and
  v) O(CO)R⁴;

2) aryl or heteroaryl, unsubstituted or substituted with one or more substituents independently selected from:
  a) $C_{1-6}$ alkyl,
  b) $C_{3-6}$ cycloalkyl,
  c) aryl, unsubstituted or substituted with 1-5 substituents each independently selected from R⁴,

- d) heteroaryl, unsubstituted or substituted with 1-5 substituents each independently selected from $R^4$,
- e) heterocycle, unsubstituted or substituted with 1-5 substituents each independently selected from $R^4$,
- f) $(F)_p C_{1-3}$ alkyl,
- g) halogen,
- h) $OR^4$,
- i) $O(CH_2)_s OR^4$,
- j) $CO_2 R^4$,
- k) $(CO)NR^{10}R^{11}$,
- l) $O(CO)NR^{10}R^{11}$,
- m) $N(R^4)(CO)NR^{10}R^{11}$,
- n) $N(R^{10})(CO)R^{11}$,
- o) $N(R^{10})(CO)OR^{11}$,
- p) $SO_2 NR^{10}R^{11}$,
- q) $N(R^{10})SO_2 R^{11}$,
- r) $S(O)_m R^{10}$,
- s) CN,
- t) $NR^{10}R^{11}$,
- u) $N(R^{10})(CO)NR^4 R^{11}$, and
- v) $O(CO)R^4$;

$R^2$ is independently selected from:

1) H, $C_0$-$C_6$ alkyl, $C_2$-$C_6$ alkenyl, $C_2$-$C_6$ alkynyl, $C_{3-6}$ cycloalkyl and heterocycle, unsubstituted or substituted with one or more substituents independently selected from:
   - a) $C_{1-6}$ alkyl,
   - b) $C_{3-6}$ cycloalkyl,
   - c) aryl, unsubstituted or substituted with 1-5 substituents each independently selected from $R^4$,
   - d) heteroaryl, unsubstituted or substituted with 1-5 substituents each independently selected from $R^4$,
   - e) heterocycle, unsubstituted or substituted with 1-5 substituents each independently selected from $R^4$,
   - f) $(F)_p C_{1-3}$ alkyl,
   - g) halogen,
   - h) $OR^4$,
   - i) $O(CH_2)_s OR^4$,
   - j) $CO_2 R^4$,
   - k) $(CO)NR^{10}R^{11}$,
   - l) $O(CO)NR^{10}R^{11}$,
   - m) $N(R^4)(CO)NR^{10}R^{11}$,
   - n) $N(R^{10})(CO)R^{11}$,
   - o) $N(R^{10})(CO)OR^{11}$,
   - p) $SO_2 NR^{10}R^{11}$,
   - q) $N(R^{10})SO_2 R^{11}$,
   - r) $S(O)_m R^{10}$,
   - s) CN,
   - t) $NR^{10}R^{11}$,
   - u) $N(R^{10})(CO)NR^4 R^{11}$, and
   - v) $O(CO)R^4$;

2) aryl or heteroaryl, unsubstituted or substituted with one or more substituents independently selected from:
   - a) $C_{1-6}$ alkyl,
   - b) $C_{3-6}$ cycloalkyl,
   - c) aryl, unsubstituted or substituted with 1-5 substituents each independently selected from $R^4$,
   - d) heteroaryl, unsubstituted or substituted with 1-5 substituents each independently selected from $R^4$,
   - e) heterocycle, unsubstituted or substituted with 1-5 substituents each independently selected from $R^4$,
   - f) $(F)_p C_{1-3}$ alkyl,
   - g) halogen,
   - h) $OR^4$,
   - i) $O(CH_2)_s OR^4$,
   - j) $CO_2 R^4$,
   - k) $(CO)NR^{10}R^{11}$,
   - l) $O(CO)NR^{10}R^{11}$,
   - m) $N(R^4)(CO)NR^{10}R^{11}$,
   - n) $N(R^{10})(CO)R^{11}$,
   - o) $N(R^{10})(CO)OR^{11}$,
   - p) $SO_2 NR^{10}R^{11}$,
   - q) $N(R^{10})SO_2 R^{11}$,
   - r) $S(O)_m R^{10}$,
   - s) CN,
   - t) $NR^{10}R^{11}$,
   - u) $N(R^{10})(CO)NR^4 R^{11}$, and
   - v) $O(CO)R^4$;

$R^{10}$ and $R^{11}$ are each independently selected from: H, $C_{1-6}$ alkyl, $(F)_p C_{1-6}$ alkyl, $C_{3-6}$ cycloalkyl, aryl, heteroaryl, and benzyl, unsubstituted or substituted with halogen, hydroxy or $C_1$-$C_6$ alkoxy, or $R^{10}$ and $R^{11}$ join to form a ring selected from: azetidinyl, pyrrolidinyl, piperidinyl, piperazinyl and morpholinyl, which ring is unsubstituted or substituted with 1-5 substituents each independently selected from $R^4$;

$R^4$ is selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

X is C or S;

Y is O, $(R^4)_2$, NCN, $NSO_2 CH_3$ or $NCONH_2$, or Y is $O_2$ when X is S;

$R^6$ is independently selected from H and:
- a) $C_{1-6}$ alkyl,
- b) $C_{3-6}$ cycloalkyl,
- c) aryl, unsubstituted or substituted with 1-5 substituents each independently selected from $R^4$,
- d) heteroaryl, unsubstituted or substituted with 1-5 substituents each independently selected from $R^4$,
- e) heterocycle, unsubstituted or substituted with 1-5 substituents each independently selected from $R^4$,
- f) $(F)_p C_{1-3}$ alkyl,
- g) halogen,
- h) $OR^4$,
- i) $O(CH_2)_s OR^4$,
- j) $CO_2 R^4$,
- k) $(CO)NR^{10}R^{11}$,
- l) $O(CO)NR^{10}R^{11}$,
- m) $N(R^4)(CO)NR^{10}R^{11}$,
- n) $N(R^{10})(CO)R^{11}$,
- o) $N(R^{10})(CO)OR^{11}$,
- p) $SO_2 NR^{10}R^{11}$,
- q) $N(R^{10})SO_2 R^{11}$,
- r) $S(O)_m R^{10}$,
- s) CN,
- t) $NR^{10}R^{11}$,
- u) $N(R^{10})(CO)NR^4 R^{11}$, and
- v) $O(CO)R^4$;

J is a bond, $C(R^6)_2$, O, or $NR^6$;

V is a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=N, $N(R^6)$—$C(R^6)_2$, N=$C(R^6)$ or $N(R^6)$—$N(R^6)$;

Q is selected from: =$C(R^{7a})$—, —$C(R^{7a})_2$—, —C(O)—, —$S(O)_m$—, =N— and —$N(R^{7a})$—;

T is selected from: =$C(R^{7b})$—, —$C(R^{7b})_2$—, —C(O)—, —$S(O)_m$—, =N— and —$N(R^{7b})$—;

$R^3$ is independently selected from H, substituted or unsubstituted $C_1$-$C_3$ alkyl, F, CN and $CO_2 R^4$;

$R^{7a}$ and $R^{7b}$ are each independently selected from $R^2$, where $R^{7a}$ and $R^{7b}$ and the atom(s) to which they are attached optionally form a ring selected from $C_{3-6}$ cycloalkyl, aryl, heterocycle, and heteroaryl, which ring is unsubstituted or substituted with 1-10 substituents where the substituents are each independently selected from $R^6$;

p is 0 to 2q+1, for a substituent with q carbons;

m is 0, 1 or 2;

s is 1, 2 or 3;

"heteroaryl" represents a stable 5- to 7-membered monocyclic- or stable 9- to 10-membered fused bicyclic heterocyclic ring system which contains an aromatic ring, any ring of which may be saturated, partially saturated, or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring;

"heterocycle" or "heterocyclic" represents a stable 5- to 7-membered monocyclic- or stable 8- to 11-membered bicyclic heterocyclic ring system which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring;

or a pharmaceutically acceptable salt or individual diastereomers thereof.

2. The compound of claim 1 having the Formula Ia:

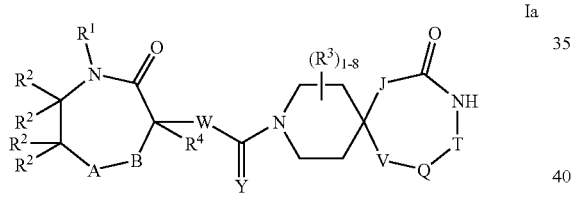

Ia wherein:

Y is O or NCN;

or a pharmaceutically acceptable salt or individual stereoisomers thereof.

3. The compound of claim 1 having the Formula Ib:

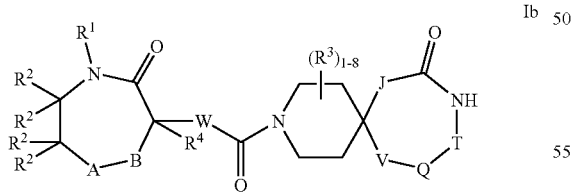

Ib or a pharmaceutically acceptable salt or individual stereoisomers thereof.

4. The compound of claim 1, wherein:

$R^1$ is selected from:

1) H, $C_1$-$C_6$ alkyl, $C_{3-6}$ cycloalkyl and heterocycle, unsubstituted or substituted with one or more substituents independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2 R^4$,
   k) CN,
   l) $NR^{10}R^{11}$, and
   m) $O(CO)R^4$; and 2) aryl or heteroaryl, unsubstituted or substituted with one or more substituents each independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) $CO_2R^4$,
   g) $(CO)NR^{10}R^{11}$,
   h) $SO_2NR^{10}R^{11}$,
   i) $N(R^{10})SO_2R^{11}$,
   j) $S(O)_m R^4$,
   k) CN,
   l) $NR^{10}R^{11}$, and,
   m) $O(CO)R^4$;

$R^2$ is selected from:

1) H, $C_0$-$C_6$ alkyl, $C_2$-$C_6$ alkynyl, $C_{3-6}$ cycloalkyl and heterocycle, unsubstituted or substituted with one or more substituents each independently selected from:
   a) $C_{1-6}$ alkyl,
   b) $C_{3-6}$ cycloalkyl,
   c) aryl, unsubstituted or substituted with 1-5 substituents each independently selected from $R^4$,
   d) heteroaryl, unsubstituted or substituted with 1-5 substituents each independently selected from $R^4$,
   e) heterocycle, unsubstituted or substituted with 1-5 substituents each independently selected from $R^4$,
   f) $(F)_p C_{1-3}$ alkyl,
   g) halogen,
   h) $OR^4$,
   i) $O(CH_2)_s OR^4$,
   j) $CO_2R^4$,
   k) $S(O)_m R^4$,
   l) CN,
   m) $NR^{10}R^{11}$, and
   n) $O(CO)R^4$; and 2) aryl or heteroaryl, unsubstituted or substituted with one more substituents independently selected from:
   a) $C_{1-6}$ alkyl,
   b) $C_{3-6}$ cycloalkyl,
   c) $(F)_p C_{1-3}$ alkyl,
   d) halogen,
   e) $OR^4$,
   f) p $CO_2R^4$,
   g) $(CO)NR^{10}R^{11}$,
   h) $SO_2NR^{10}R^{11}$,
   i) $N(R^{10})SO_2R^{11}$,
   j) $S(O)_m R^4$,
   k) CN,
   l) $NR^{10}R^{11}$, and
   m) $O(CO)R^4$, $R^{10}$ and $R^{11}$ are independently selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally join to form a ring selected from: azetidinyl, pyrrolidinyl, piperidinyl, piperazinyl and morpholinyl, which ring is unsubstituted or substituted with 1-5 substituents each independently selected from $R^4$;

$R^4$, is selected from: H, $C_{1-6}$ alkyl, $(F)_pC_{1-6}$ alkyl, $C_{3-6}$ cycloalkyl, aryl, heteroaryl and benzyl, unsubstituted or substituted with halogen, hydroxy or $C_1$-$C_6$ alkoxy;

W is O, $NR^4$ or $C(R^4)_2$;

$R^6$ is independently selected from H and:
- a) $C_{1-6}$ alkyl,
- b) $C_{3-6}$ cycloalkyl,
- c) $(F)_pC_{1-3}$ alkyl,
- d) halogen,
- e) $OR^4$,
- f) $CO_2R^4$,
- g) $(CO)NR^{10}R^{11}$,
- h) $SO_2NR^{10}R^{11}$,
- i) $N(R^{10})SO_2R^{11}$,
- j) $S(O)_mR^4$,
- k) CN,
- l) $NR^{10}R^{11}$, and
- m) $O(CO)R^4$; and J is a bond and V is a bond and T is C(=O)—, or
J is a bond and V is a bond, or
J is a bond and, V is a bond, $C(R^6)_2$, O, $S(O)_m$, $NR^6$, $C(R^6)_2$—$C(R^6)_2$, $C(R^6)$=$C(R^6)$, $C(R^6)_2$—$N(R^6)$, $C(R^6)$=N, $N(R^6)$—$C(R^6)_2$, N=$C(R^6)$ or $N(R^6)$—N$(R^6)$, or
V is a bond and J is a bond, $C(R^5)_2$, O, $S(O)_m$ or $NR^5$;

Q is selected from:
- (1) =$C(R^{7a})$—,
- (2) —$C(R^{7a})_2$—,
- (3) —C(=O)—,
- (4) —$S(O)_m$—,
- (5) =N—, and
- (6) —$N(R^{7a})$—;

T is selected from:
- (1) =$C(R^{7b})$—,
- (2) —$C(R^{7b})_2$—,
- (3) —C(=O)—,
- (4) —$S(O)_m$—,
- (5) =N—, and
- (6) —$N(R^{7b})$—;

each $R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom(s) to which they are attached optionally join to form a ring selected from $C_{3-6}$cycloalkyl, aryl, heterocycle, and heteroaryl, which ring is unsubstituted or substituted with 1-10 substituents each independently selected from $R^6$;

p is 0 to 2q+1, for a substituent with q carbons
m is 0 to 2;
s is 1 to 3;
or a pharmaceutically acceptable salt or individual stereoisomers thereof.

5. The compound of claim 1, wherein:
$R^1$ is selected from:
1) H, $C_1$-$C_6$ alkyl, $C_{3-6}$ cycloalkyl and heterocycle, unsubstituted or substituted with one or more substituents each independently selected from:
- a) $C_{1-6}$ alkyl,
- b) $C_{3-6}$ cycloalkyl,
- c) phenyl, unsubstituted or substituted with 1-5 substituents each independently selected from $R^4$,
- d) heteroaryl, unsubstituted or substituted with 1-5 substituents each independently selected from $R^4$, where heteroaryl is selected from:
  imidazole, isoxazole, oxazole, pyrazine, pyrazole, pyridazine, pyridine, pyrimidine, and thiazole;
- e) heterocycle, unsubstituted or substituted with 1-5 substituents each independently selected from $R^4$, where heterocycle is selected from:
  azetidine, dioxane, dioxolane, morpholine, oxetane, piperazine, piperidine, pyrrolidine, tetrahydrofuran, and tetrahydropyran;
- f) $(F)_pC_{1-3}$ alkyl,
- g) halogen,
- h) $OR^4$,
- i) $O(CH_2)_sOR^4$,
- j) $CO_2R^4$,
- k) CN,
- l) $NR^{10}R^{11}$,
- m) $O(CO)R^4$;

2) aryl or heteroaryl, selected from: phenyl, imidazole, isoxazole, oxazole, pyrazine, pyrazole, pyridazine, pyridine, pyrimidine, and thiazole, unsubstituted or substituted with one or more substituents each independently selected from:
- a) $C_{1-6}$ alkyl,
- b) $C_{3-6}$ cycloalkyl,
- c) $(F)_pC_{1-3}$ alkyl,
- d) halogen,
- e) $OR^4$,
- f) $CO_2R^4$,
- g) $(CO)NR^{10}R^{11}$,
- h) $SO_2NR^{10}R^{11}$,
- i) $N(R^{10})SO_2R^{11}$,
- j) $S(O)_mR^4$,
- k) CN,
- l) $NR^{10}R^{11}$, and
- m) $O(CO)R^4$;

$R^2$ is selected from:
1) H, $C_0$-$C_6$ alkyl, $C_{3-6}$ cycloalkyl and heterocycle, unsubstituted or substituted with one or more substituents each independently selected from:
- a) $C_{1-6}$ alkyl,
- b) $C_{3-6}$ cycloalkyl,
- c) phenyl, unsubstituted or substituted with 1-5 substituents each independently selected from $R^4$,
- d) heteroaryl, unsubstituted or substituted with 1-5 substituents each independently selected from $R^4$, where heteroaryl is selected from: benzimidazole, benzothiophene, furan, imidazole, indole, isoxazole, oxazole, pyrazine, pyrazole, pyridazine, pyridine, pyrimidine, pyrrole, thiazole, thiophene, and triazole;
- e) heterocycle, unsubstituted or substituted with 1-5 substituents each independently selected from $R^4$, and where heterocycle is selected from: azetidine, imidazolidine, imidazoline, isoxazoline, isoxazolidine, morpholine, oxazoline, oxazolidine, oxetane, pyrazolidine, pyrazoline, pyrroline, tetrahydrofuran, tetrahydropyran, thiazoline, and thiazolidine;
- f) $(F)_pC_{1-3}$ alkyl,
- g) halogen,
- h) $OR^4$,
- i) $O(CH_2)_sOR^4$,
- j) $CO_2R^4$,
- k) CN,
- l) $NR^{10}R^{11}$, and
- m) $O(CO)R^4$; and 2) aryl or heteroaryl, selected from: phenyl, benzimidazole, benzothiophene, furan, imidazole, indole, isoxazole, oxazole, pyrazine, pyrazole, pyridazine, pyridine, pyrimidine, pyrrole, thiazole, thiophene, and triazole, where said aryl or heteroaryl is unsubstituted or substituted with one or more substituents each independently selected from:
a) $C_{1-6}$ alkyl,
b) $C_{3-6}$ cycloalkyl,
c) $(F)_p C_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_m R^4$,
k) CN,
l) $NR^{10}R^{11}$, and
m) $O(CO)R^4$, $R^{10}$ and $R^{11}$ are each independently selected from: H, $C_{1-6}$ alkyl, $(F)_p C_{1-6}$ alkyl, $C_{3-6}$ cycloalkyl, aryl, heteroaryl and benzyl, unsubstituted or substituted with halogen, hydroxy or $C_1$-$C_6$ alkoxy, where $R^{10}$ and $R^{11}$ optionally joined to form a ring selected from: azetidinyl, pyrrolidinyl, piperidinyl, piperazinyl and morpholinyl, which is unsubstituted or substituted with 1-5 substituents each independently selected from $R^4$;

$R^4$ is independently selected from: H, $C_{1-6}$ alkyl, $(F)_p C_{1-6}$ alkyl, $C_{3-6}$ cycloalkyl, aryl, heteroaryl and phenyl, unsubstituted or substituted with hydroxy or $C_1$-$C_6$ alkoxy;

W is $NR^4$ or $C(R^4)_2$;

J is a bond, V is a bond, Q is $—N(R^{7a})—$, and T is $—C(=O)—$ or

J is a bond, V is a bond, Q is $—N=$, and T is $=C(R^{7b})—$, or

J is a bond, V is a bond, Q is $—C(R^{7a})_2—$, and T is $—C(R^{7b})_2—$, or

J is a bond, V is a bond, Q is $—C(R^{7a})=$, T is $=C(R^{7b})—$, and the atoms to which $R^{7a}$ and $R^{7b}$ are attached are joined together to form a benzene, pyridine, or diazine ring, or J is a bond, V is $C(R^6)_2$, Q is $—C(R^{7a})=$, T is $=C(R^{7b})—$, and the atoms to which $R^{7a}$ and $R^{7b}$ are attached are joined together to form a benzene, or pyridine ring, or J is O, V is a bond, Q is $—C(R^{7a})=$, T is $=C(R^{7b})—$, and the atoms to which $R^{7a}$ and $R^{7b}$ are attached are joined together to form a benzene, or pyridine;

$R^6$ is independently selected from H and:
a) $C_{1-6}$ alkyl,
b) $C_{3-6}$ cycloalkyl,
c) $(F)_p C_{1-3}$ alkyl,
d) halogen,
e) $OR^4$,
f) $CO_2R^4$,
g) $(CO)NR^{10}R^{11}$,
h) $SO_2NR^{10}R^{11}$,
i) $N(R^{10})SO_2R^{11}$,
j) $S(O)_m R^4$,
k) CN,
l) $NR^{10}R^{11}$, and
m) $O(CO)R^4$;

each $R^3$ is independently selected from H, substituted or unsubstituted $C_1$-$C_3$ alkyl, F, CN and $CO_2R^4$;

$R^{7a}$ and $R^{7b}$ are each independently selected from $R^2$, where $R^{7a}$ and $R^{7b}$ and the atom(s) to which they are attached optionally join to form a ring selected from $C_{3-6}$ cycloalkyl, aryl, heterocycle, and heteroaryl, which ring is unsubstituted or substituted with 1-10 substituents each independently selected from $R^6$;

p is 0 to 2q+1, for a substituent with q carbons m is 0 to 2;

s is 1 to 3;

or a pharmaceutically acceptable salt or individual stereoisomers thereof.

6. A compound selected from:

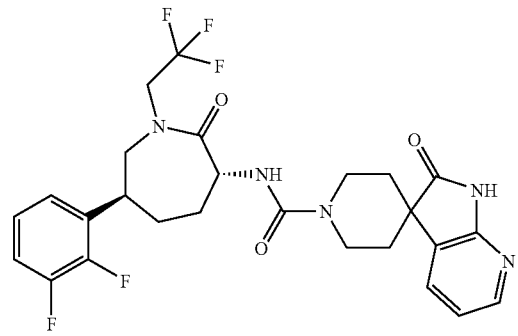

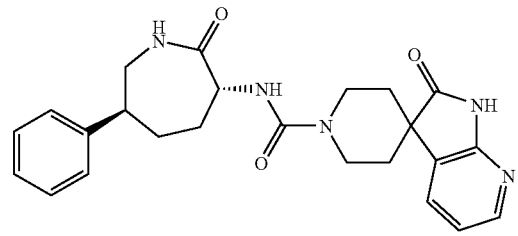

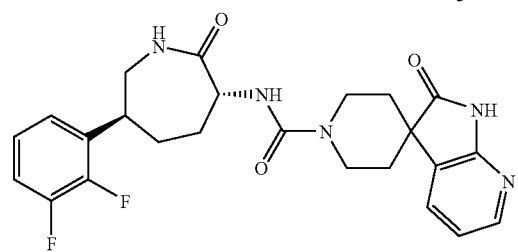

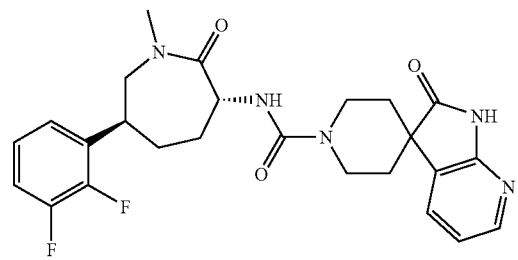

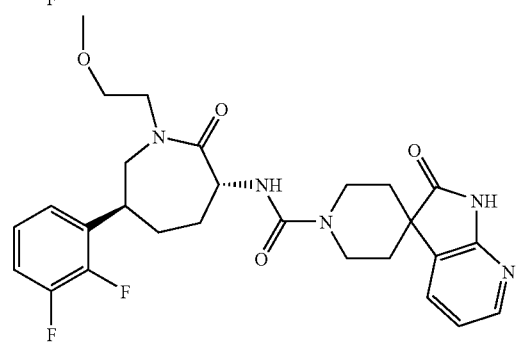

75
-continued
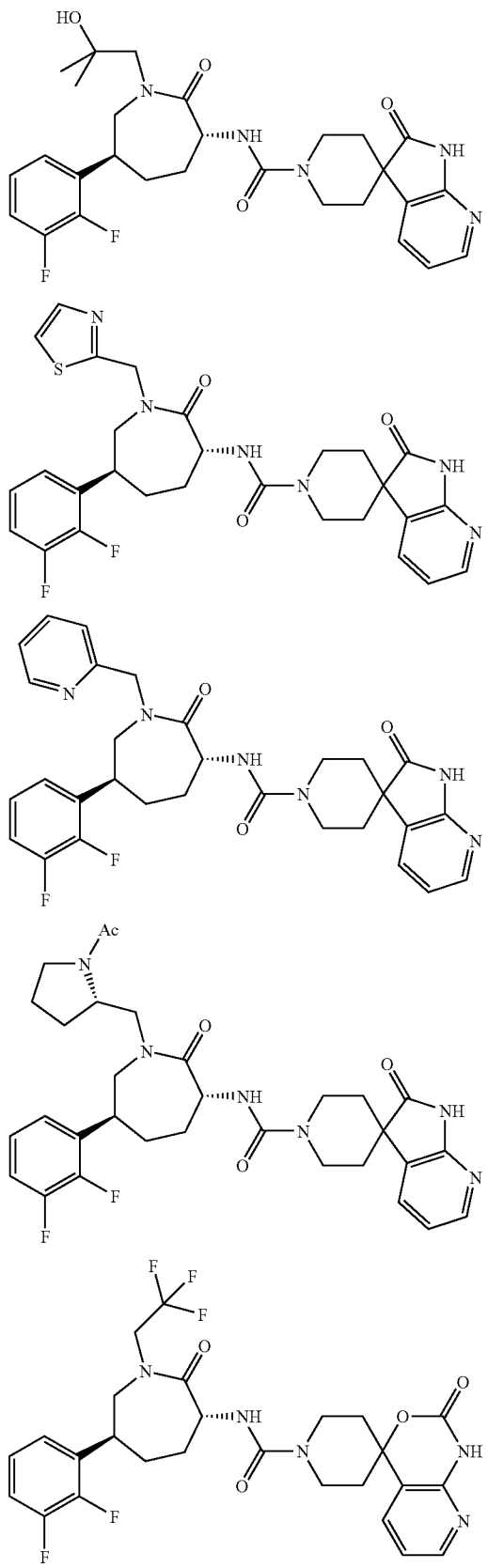
76
-continued
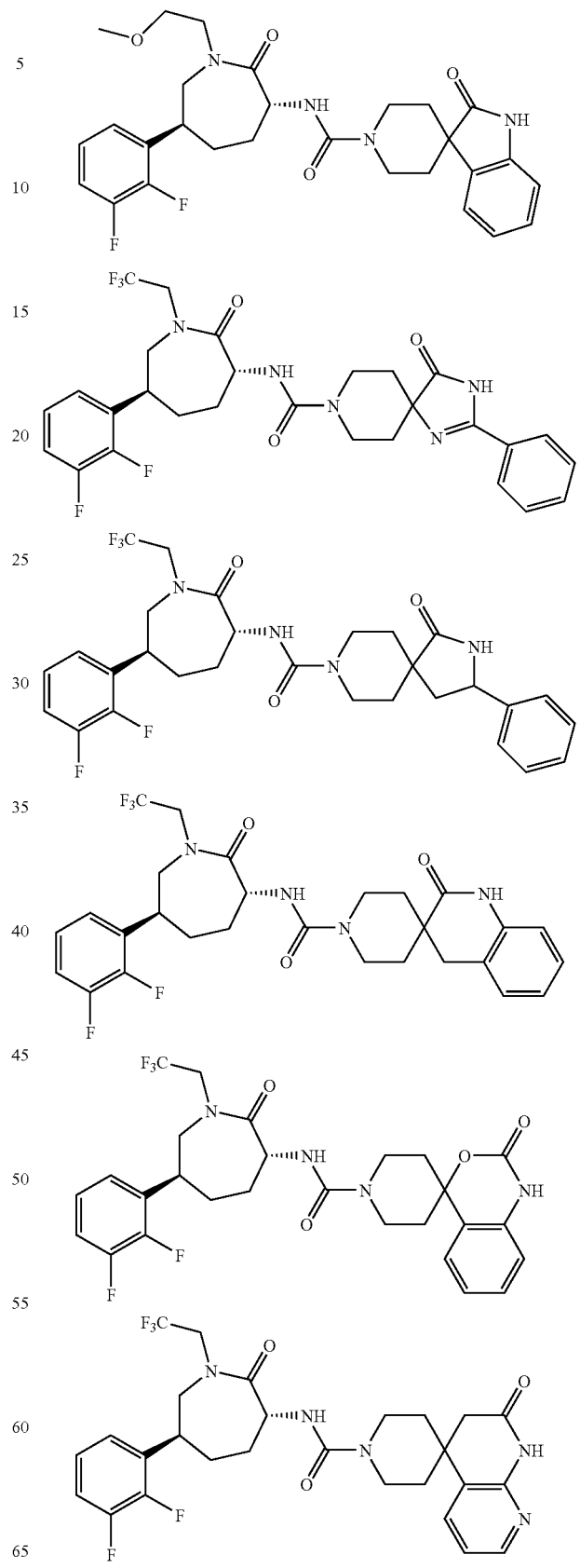

-continued
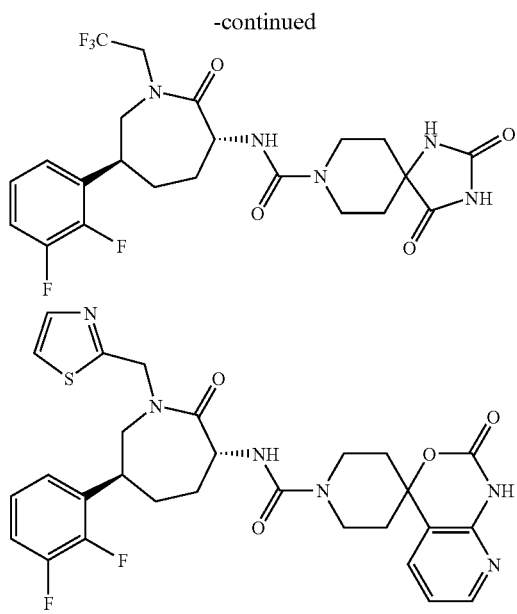
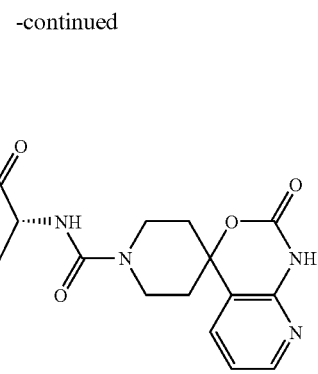
or a pharmaceutically acceptable salt or individual diastereomers thereof.
7. A pharmaceutical composition which comprises an inert carrier and the compound of claim 1.
* * * * *